United States Patent
Krasnov et al.

(10) Patent No.: US 11,445,925 B2
(45) Date of Patent: Sep. 20, 2022

(54) PRESSURE OF BLOOD MONITOR

(71) Applicants: Andrey Krasnov, Brooklyn, NY (US);
Victor Krasnov, Tarzana, CA (US);
Victor I. Gezunterman, New York, NY (US)

(72) Inventors: Andrey Krasnov, Brooklyn, NY (US);
Victor Krasnov, Tarzana, CA (US);
Victor I. Gezunterman, New York, NY (US)

( * ) Notice: Subject to any disclaimer, the term of this patent is extended or adjusted under 35 U.S.C. 154(b) by 625 days.

(21) Appl. No.: 14/673,853

(22) Filed: Mar. 30, 2015

(65) Prior Publication Data
US 2015/0272455 A1  Oct. 1, 2015

Related U.S. Application Data

(60) Provisional application No. 61/971,947, filed on Mar. 28, 2014.

(51) Int. Cl.
| A61B 5/022 | (2006.01) |
| A61B 5/021 | (2006.01) |
| A61B 5/0205 | (2006.01) |
| A61B 5/00 | (2006.01) |

(52) U.S. Cl.
CPC ........ *A61B 5/02241* (2013.01); *A61B 5/0205* (2013.01); *A61B 5/02108* (2013.01); *A61B 5/683* (2013.01); *A61B 5/6826* (2013.01); *A61B 5/7278* (2013.01)

(58) Field of Classification Search
CPC ............ A61B 5/02108; A61B 5/02241; A61B 5/6826; A61B 2562/0214; A61B 5/021
See application file for complete search history.

(56) References Cited

U.S. PATENT DOCUMENTS

| 5,511,551 A | * | 4/1996 | Sano | A61S 5/02241 600/499 |
| 6,443,906 B1 | * | 9/2002 | Ting | A61B 5/681 600/490 |
| 2003/0036690 A1 | * | 2/2003 | Geddes | A61B 5/02233 600/323 |
| 2008/0076995 A1 | * | 3/2008 | Hoarau | A61S 5/14552 600/344 |
| 2008/0171915 A1 | * | 7/2008 | Kawajiri | A61B 5/02241 600/300 |

(Continued)

OTHER PUBLICATIONS

Guelen et al., "Finometer, finger pressure measurements with the possibility to reconstruct brachial pressure", Blood Pressure Monitoring, vol. 8, Feb. 2003, pp. 27-30.

(Continued)

*Primary Examiner* — Allen Porter
*Assistant Examiner* — Michael A Catina
(74) *Attorney, Agent, or Firm* — Kolitch Romano LLP

(57) ABSTRACT

A method for monitoring pressure of blood in an artery may include contacting a non-invasive sensor of a pressure of blood monitoring device at an area above an artery of a finger, collecting with the sensor one or more pressure data readings, other than readings corresponding to an air pressure reading, from the area after the contacting and after a pressure is exerted at the area on the sensor; and analyzing with a computing device the one or more pressure data readings to generate at least one of a blood pressure reading and a heart pulse reading.

21 Claims, 18 Drawing Sheets

(56) References Cited

U.S. PATENT DOCUMENTS

| | | | | |
|---|---|---|---|---|
| 2010/0107770 A1* | 5/2010 | Serban | .................... | G01L 1/142 |
| | | | | 73/718 |
| 2015/0031964 A1* | 1/2015 | Bly | ...................... | A61B 5/7465 |
| | | | | 600/301 |
| 2015/0157269 A1* | 6/2015 | Lisogurski | ........... | A61B 5/0205 |
| | | | | 600/301 |

OTHER PUBLICATIONS

Bogert et al., "Non-invasive pulsatile arterial pressure and stroke volume changes from the human finger", Experimental Physiology, vol. 90, Issue 4, Mar. 31, 2005, pp. 437-446.

Setra Blog, "8 Operating Features of Capacitance Based Transducers", http://blog.setra.com/8-operating-features-capacitance-based-transducers/2012/10/24, Oct. 24, 2012, retrieved May 19, 2015.

EMPA Materials Science & Technology, "Wristband revolutionises blood pressure measurement", Press Release, Jun. 12, 2013.

* cited by examiner

PRESSURE OF BLOOD MONITOR

CROSS-REFERENCE TO RELATED APPLICATION

This application claims the benefit of U.S. Provisional Patent Application Ser. No. 61/971,947 filed Mar. 28, 2014 and entitled "Blood Pressure Monitor." The complete disclosure of the above provisional application is hereby incorporated by reference for all purposes.

INTRODUCTION

Existing methods of measuring blood pressure on a digit (such as a finger) in outpatient settings typically employ the same underlying technology as used in arm and wrist blood pressure measurement devices. As such, these devices typically require a spacious interior to house an inflatable cuff and multiple batteries or other power sources necessary for cuff inflation. These methods are therefore generally not suitable for frequent, on demand use due to their relatively large size and the time it takes to inflate the cuff. What is needed is a more convenient blood pressure monitoring device that is less cumbersome and more suitable for discrete, frequent use and/or continuous monitoring. Ideally, an improved blood pressure measuring device would also have a reduced cost of manufacturing.

SUMMARY

The present disclosure may include one or more apparatus, systems, and methods related to monitoring of pressure, including monitoring the pressure of blood.

An embodiment of the present disclosure may include a method for monitoring pressure of blood in an artery that may include contacting a non-invasive sensor of a pressure of blood monitoring device at an area above an artery of a finger, collecting with the capacitive sensor one or more pressure data readings, other than readings corresponding to an air pressure reading, from the area after the contacting and after a pressure is exerted at the area on the sensor; and analyzing with a computing device the one or more pressure data readings to generate at least one of a blood pressure reading and a heart pulse reading.

An embodiment of the present disclosure may include a method for monitoring pressure of blood in an artery that may include contacting a capacitive sensor of a blood pressure monitoring device at an area of a body capable of being monitored for pressure of blood readings, collecting with the non-inflatable sensor one or more pressure of blood data readings from the area after the contacting and after a pressure is exerted at the area on the sensor; and analyzing with a computer device one or more pressure data readings to generate one or more health data readings based on an analysis of the one or more pressure data readings.

An embodiment of the present disclosure may include a system to monitor the pressure of blood that may include a monitoring device that includes a capacitive sensor, the capacitive sensor being configured to be in contact with an area of skin above an artery. The capacitive sensor may include a conductive element disposed on a bottom side adjacent a printed circuit board, a resilient member, an insulation layer separating the conductive element from the resilient member, and an adhesive layer covering the resilient member, wherein the capacitive sensor is configured to collect one or more pressure of blood data readings while in contact with the area. The system may also include a data processing device, in communication with the capacitive sensor, configured to analyze data readings produced by the sensor, the data processing device including a processor, a memory, and a set of instructions stored in the memory and executed by the processor to determine whether the information provided by the sensor meets selected criteria, and providing an alert to a user if the information meets the criteria.

BRIEF DESCRIPTION OF THE DRAWINGS

Advantages and characteristics of one or more embodiments of the present disclosure will become apparent from the description with reference to the figures.

DETAILED DESCRIPTION

Overview

Various embodiments of pressure of blood monitoring devices, one or more embodiments including a non-inflating, digit-mounted blood pressure of blood monitor, are described below and illustrated in the associated drawings. Unless otherwise specified, a pressure of blood monitor and/or its various components may, but are not required to, contain at least one of the structure, components, functionality, and/or variations described, illustrated, and/or incorporated herein. Furthermore, the structures, components, functionalities, and/or variations described, illustrated, and/or incorporated herein in connection with a pressure of blood monitor may, but are not required to, be included in other pressure of blood monitors. The following description of various embodiments is merely exemplary in nature and is in no way intended to limit the invention, its application or uses. Additionally, the advantages provided by the embodiments, as described below, are illustrative in nature and not all embodiments provide the same advantages or the same degree of advantages.

This disclosure concerns a monitoring device that measures pressure of blood (interchangeably termed "BP" for blood pressure) non-invasively on a user's finger. A BP monitor, according to aspects of the present disclosure, includes a non-inflatable cuff and enables BP devices that are much smaller in size, less expensive to make, and potentially more precise than traditional finger-mounted BP devices. In addition, the embodiments described herein can incorporate several types of sensors to measure blood pressure either on demand or continuously, or both. In some examples, systolic and diastolic values may be generated on demand similar to traditional monitors. In some examples, continuous monitoring and alerting of patients of unwanted blood pressure levels may be provided. In one or more embodiments, the BD device readings can be used to generate a heart pulse reading based on one more readings of oscillations of pressure of blood.

Definitions

Blood pressure is typically stated in terms of two numbers, e.g. "110 over 70" or "115/75." These two numbers correspond to systolic and diastolic blood pressure, respectively.

"Systolic pressure" is the blood pressure caused by a contracting heart, pushing blood through the arteries. Normal systolic blood pressure is less than 120 mm Hg.

"Diastolic pressure" is the pressure in the arteries during the time between contractions, i.e., when the heart is resting. Normal diastolic blood pressure is less than 80 mm Hg.

A "sphygmomanometer" is a device for measuring blood pressure.

SPECIFIC EXAMPLES, MAJOR COMPONENTS, AND ALTERNATIVES

Example 1

Figure 1:
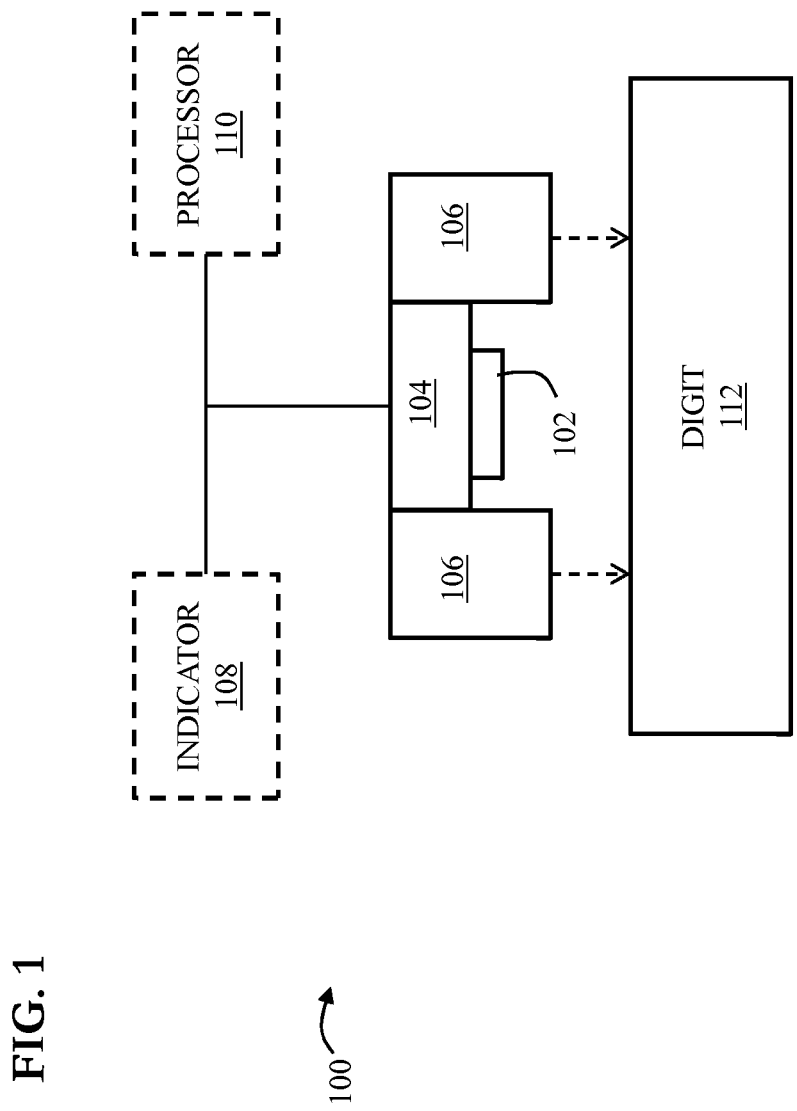
FIG. 1 is a schematic diagram showing relationships between components of an illustrative pressure of blood monitoring device.

This example describes an illustrative digit-mounted BP monitoring device generally indicated at 100; see FIG. 1.

FIG. 1 is a schematic diagram showing relationships between various components that may be included in BP monitoring device 100. In this example, BP monitor 100 may include a sensor 102, a sensor mount 104, a brace 106, an indicator 108, and/or a processor 110, and may be configured to be applied to a digit 112, such as a human finger.

Sensor 102 may include one or more suitable sensors configured to sense and/or measure one or more desired physical or physiological characteristics when placed adjacent to an area of the body, for example, a digit 112 and convert the information into a useable format such as an electrical and/or digital signal. For example, sensor 102 may include a device sensitive to pressure, pulse, sound, light, motion, temperature, chemical composition or changes, electromagnetic fields, moisture, vibration, oscillation, and/or any combination of these. In some examples, sensor 102 may include an electronic sensor. In some examples, sensor 102 may include a mechanical sensor. In some examples, sensor 102 may include a selectable sensitivity feature.

Sensor 102 may be affixed, attached, operatively connected, or otherwise retained by sensor mount 104. Sensor mount 104 may include any suitable structure configured to ensure sensor 102 is held adjacent to an area of the body to be monitored, such as digit 112, in a predetermined manner suitable for the sensor type and configuration. For example, many possible sensors will need to be held in a fixed position such that pressure placed on the sensor by the digit does not displace the sensor relative to sensor mount 104. In other examples, sensor 102 may be mounted to sensor mount 104 in a floating or biased fashion, such that the sensor may move by a certain amount when held against digit 112. In some examples, an amount of such biasing may be adjustable or selectable. In some examples, sensor 102 may be fixed in one dimension and adjustable in one or more other dimensions, resulting in a predetermined number of degrees of freedom. For example, sensor mount 104 may be configured such that sensor 102 is fixed in a direction normal to digit 112, but may be adjusted along a path parallel to the digit.

Figure 3:
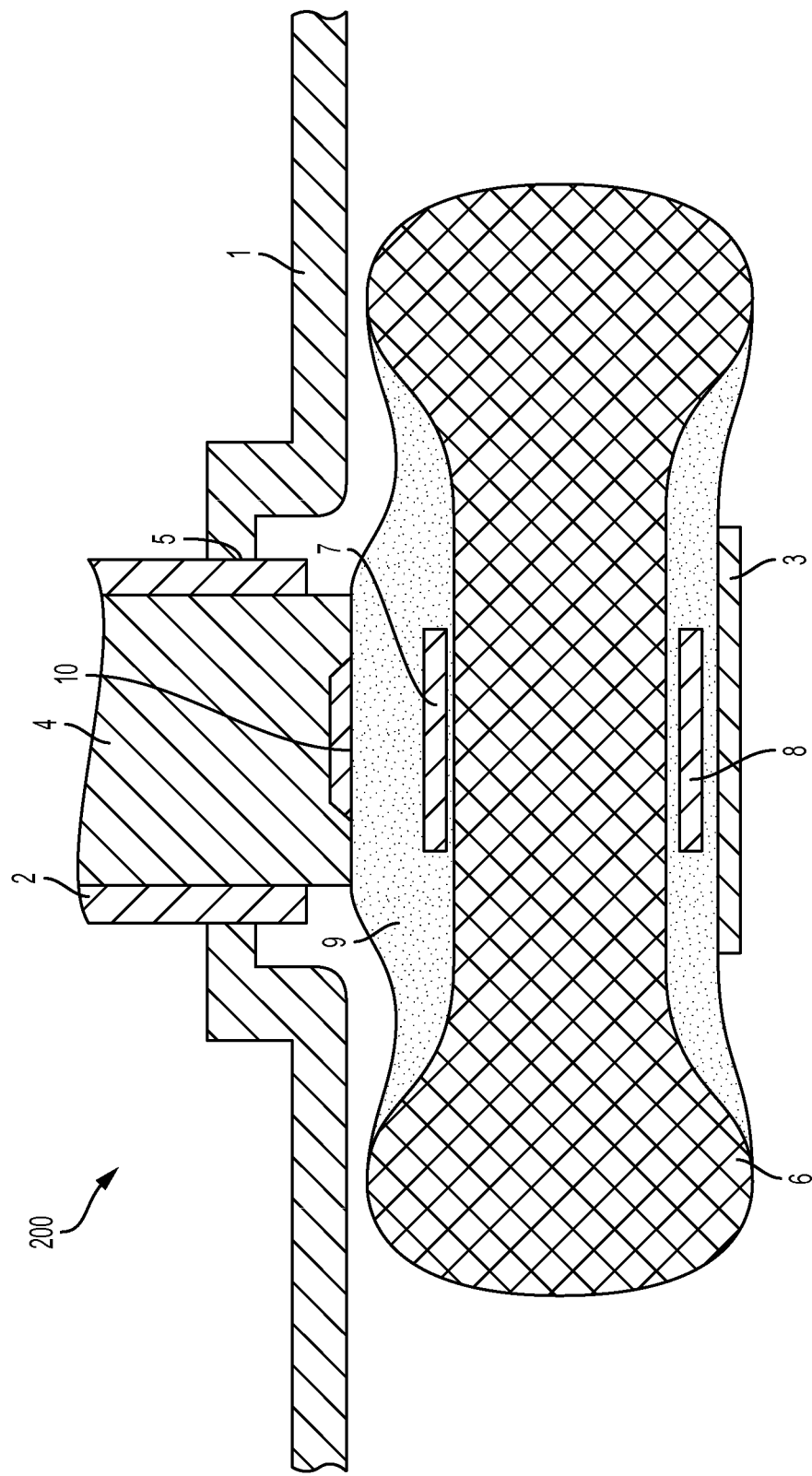
FIG. 3 is a sectional overhead view of the device of FIG. 2, including a portion of a human finger.
Figure 4:
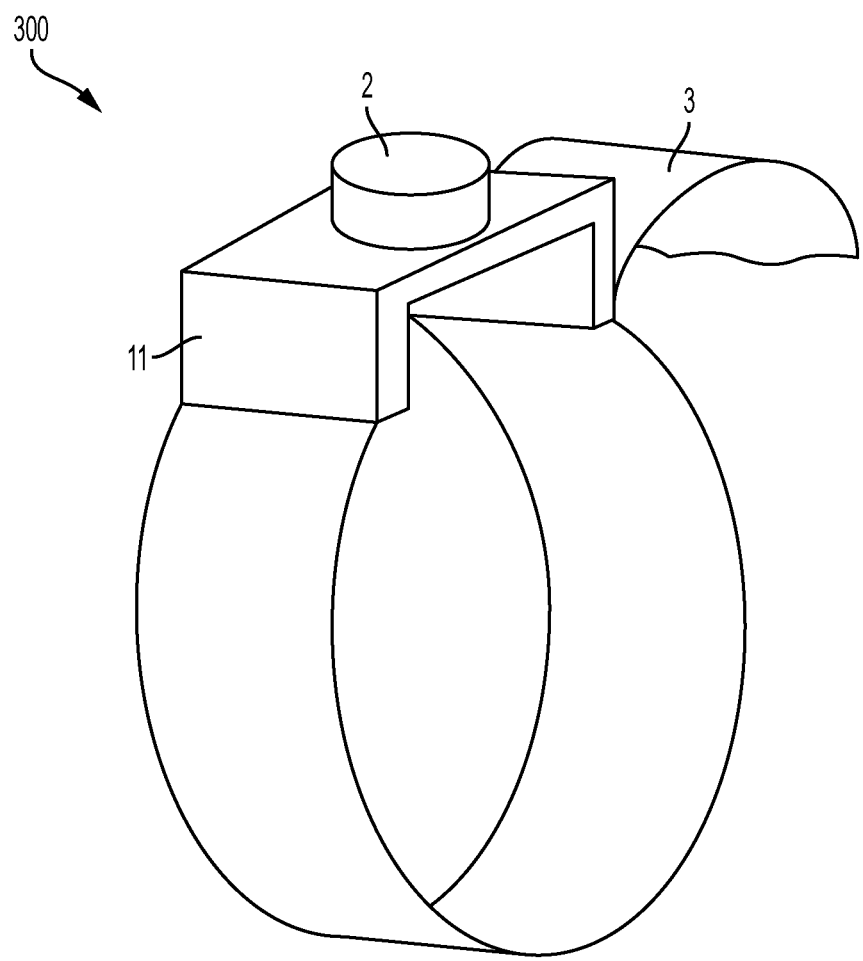
FIG. 4 is an isometric view of another illustrative pressure of blood monitoring device having a crosswise brace portion.

Brace 106 may surround, attach piecewise, and/or extend from sensor mount 104, and may include any suitable structure configured to brace BP monitor 100 against certain portions of the anatomy of digit 112. Brace 106 may be configured to create a void or space under sensor 102. For example, brace 106 may include a pair of elongate extensions with one extension on either side of sensor mount 104. Brace 106 may be sized and configured such that the brace has a long axis aligned with the long axis of digit 112, and spans the distance between opposite terminal condyles of a phalanx bone in the digit (as shown in FIG. 3). In some examples, brace 106 has a long axis aligned perpendicular to the long axis of the digit, and may be sized to span a portion of the width of the digit (as shown in FIG. 4). In these examples, a functional portion of brace 106 may have a width smaller than an expected diameter of digit 112.

Indicator 108 may include any suitable human-perceptible indicator configured to provide information related to the functioning of BP monitor 100. For example, indicator 108 may include one or more audible, visual, and/or tactile features. Indicator 108 may include a digital display, a light or LED, a speaker, a positional indicator, a color indicator, a pop-up button, a vibrating component, and/or the like, and/or any combination of these. In some examples, indicator 108 may be excluded from the device.

Processor 110 may include any suitable data processing device or controller (as further described below), and may be configured to respond to information provided by sensor 102. For example, processor 110 may be programmed or configured to respond to pressure above a certain setpoint by turning on an LED indicator 108 and/or displaying a textual or numeric value on a display indicator 108. Processor 110 may include aspects capable of receiving inputs and/or adjustments from a user through a user interface. For example, processor 110 may be connectable to another device having a graphical user interface and an input device through which various aspects and/or setpoints of BP monitor 100 may be selected and/or adjusted. In some examples, setpoints may be adjusted by mechanical interfaces on BP monitor 100 itself. In some examples, processor 110 may be excluded and an output of sensor 102 may directly control indicator 108.

Various embodiments of BP monitor 100 are described in detail below, along with related concepts and methods.

Example 2

Figure 2:
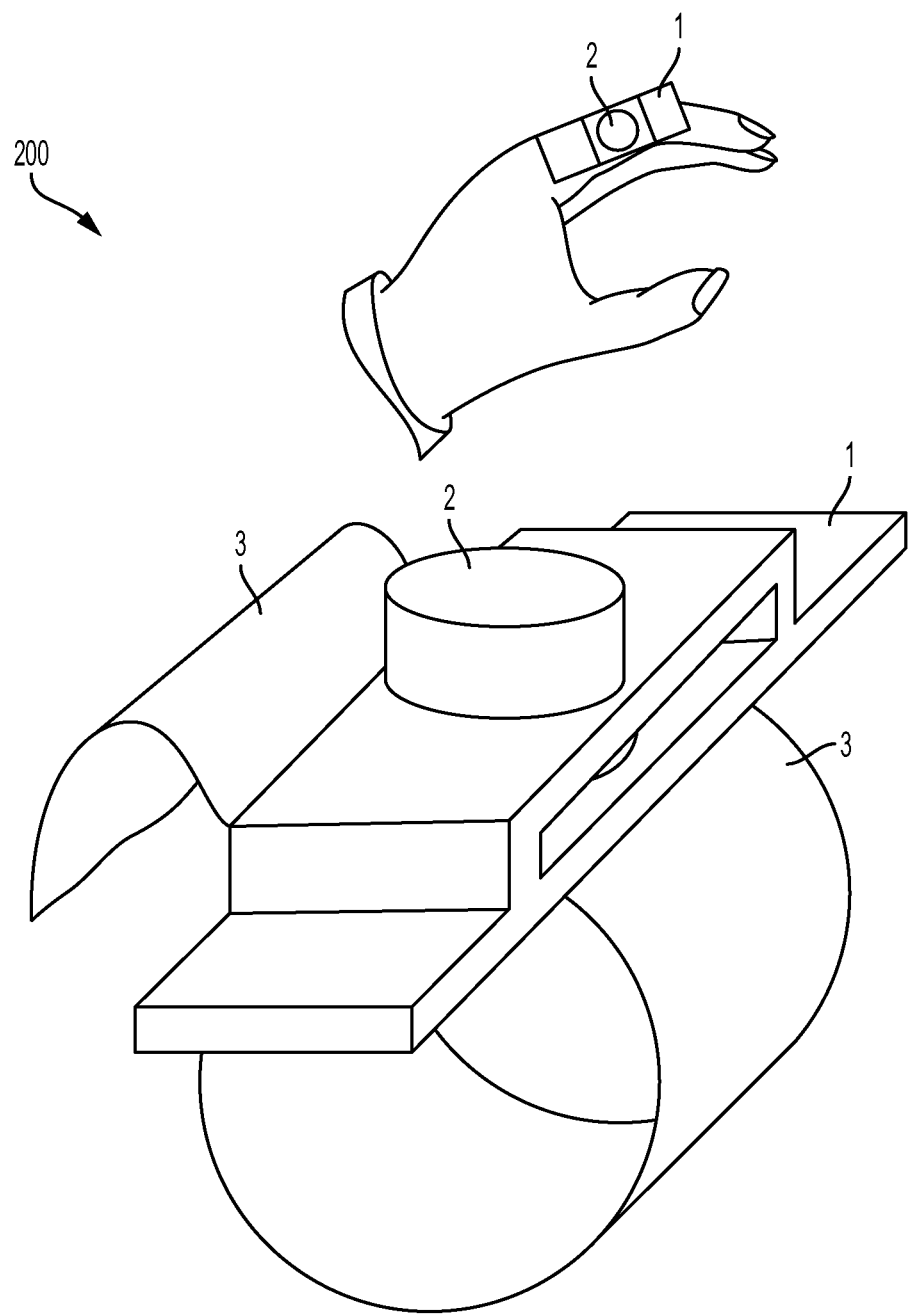
FIG. 2 is an isometric view of an illustrative pressure of blood monitoring device according to aspects of the present disclosure, and a side view of the device mounted on a finger.

This example describes an illustrative BP monitoring device 200 having an elongate brace portion, the device configured to be placed on the side of a finger; see FIGS. 2-3.

In this example, BP monitor 200 may include a brace in the form of a flat panel 1 which may have a sensor mount in the form of a cylindrical chamber 2 screwed or otherwise fixed into the panel. Chamber 2 may house sensors, and a height of the chamber may be adjustable to change position of a sensor relative to the finger. Panel 1 may include a non-stretchable strap 3 affixed to the panel at one end, and a lock mechanism (not shown) for the other end of the strap. Strap 3 may be any suitable strap or other attachment device configured to secure monitor 200 to a finger. Monitor 200 may be used on any finger, and may preferably be used on an index finger as shown in the top drawing of FIG. 2. As indicated, monitor 200 may be configured to attach to a side of the finger.

FIG. 3 shows a cross-section of the device mounted on a finger, from a lateral view. Panel 1 may be supported by the widening of a phalanx bone 6 in the joint areas of fingers (i.e., at the condyles) and holds cylindrical chamber 2 off the bone, between the joints. In this example, chamber 2 may house a sensor insert 4 with sensors on its surface coming in contact with a skin 10 of the finger. Proximity of sensor insert 4 to the skin can be adjusted via a screw thread 5 on the chamber to accommodate the particular anatomy of a patient. To perform measurement, strap 3 may be wrapped around the finger in a snug but comfortable fashion. Pressure is then created in a soft tissue 9 of the finger, causing the tissue to fill the space under the strap (in this case around a radial artery 7). Pressure may be created in soft tissue 9 by bending the finger or otherwise pressing on the surface under the strap. Note that finger-bend can create sufficient enough pressure to occlude finger arteries even for very high systolic levels (e.g., 300 mm Hg).

Ulnar artery 8 can also be used to perform measurement, if the device is flipped to the other side of the finger or with sensor installed on the medial side of the finger. Outside pressure does not need to be necessarily provided by bending the finger. If the device is configured to operate in the continuous monitoring mode, constant outside pressure can be provided by a special piston under spring pressure, as further explained below.

Example 3

This example describes an illustrative BP monitoring device 300 having a short cross-brace portion, the device configured to be placed on a finger similar to a ring; see FIG. 4.

BP monitor 300 is a variation of monitor 200, akin to a ring in which sensor housing 2 and strap 3 may be held by a bracket 11 that is smaller in width than the finger, thereby preventing the soft tissue of a finger from filling the space under the bracket. Rather, soft tissue may be allowed to fill the space under the sensors when the finger is bent. In general, monitor 300 may be operated in substantially the same manner as monitor 200.

Example 4

Figure 5:
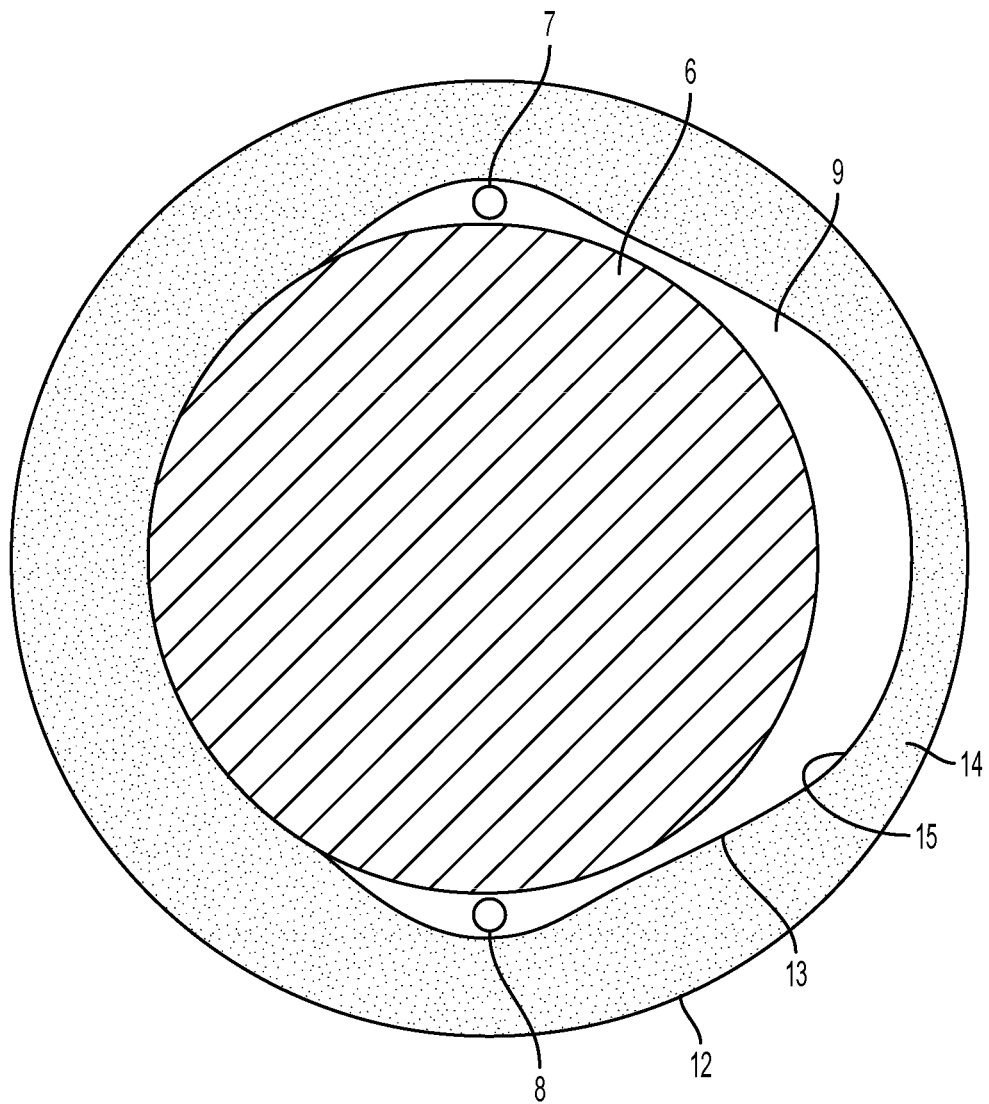
FIG. 5 is a sectional view of an illustrative prior art inflatable cuff-style blood pressure device on a finger.

This example describes shortcomings of an existing method used in traditional BP monitoring devices; see FIG. 5.

FIG. 5 illustrates one of the main shortcomings of using a prior art inflatable cuff to measure blood pressure in a finger. In FIG. 5, outer 12 and inner 13 surfaces of the cuff are shown with the cuff inflated by a volume of air 14, where reference number 15 is the surface of the finger. As shown, soft tissue 9 may accumulate in an area spaced from the arteries (7 and 8), resulting in insufficient soft tissue around the finger arteries, so the arteries are pressed down against the bone. This configuration can result in incorrect measurement of blood pressure, as the pressure applied from the outside via inflation of the cuff may not be equal to the pressure inside the arteries.

Example 5

Figure 6:
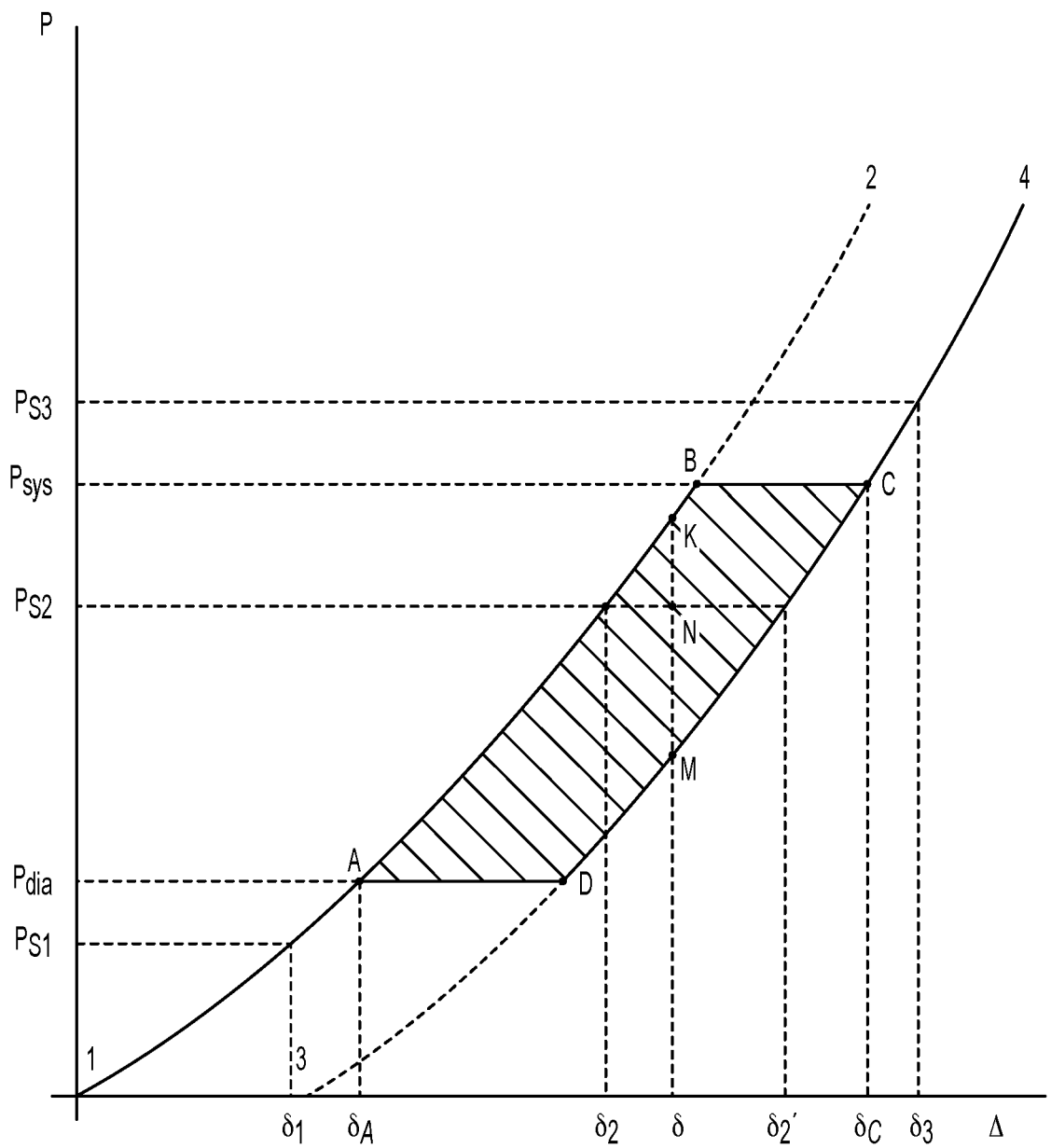
FIG. 6 depicts response curves showing relationships between the quantified change in an outside parameter responsible for pressure changing in the soft tissue surrounding an artery and the corresponding tissue pressure or pressure on the artery.

This example describes expected response curves when applying pressure to the tissue around an artery; see FIG. 6.

In addition to the device architecture described throughout this disclosure, sensor designs may also be varied to accommodate various modes of use. Various sensors can be used separately or in combination. In some examples, sensor designs are based on the oscillometric method. FIG. 6 is a diagram depicting the concept underlying oscillations measured by these sensor designs.

Referring to FIG. 6, the horizontal, or "X" axis signifies the quantified change in an outside parameter responsible for pressure changing in the soft tissue surrounding an artery. In traditional devices, outside pressure is usually created by pumping air into a cuff, whereas this disclosure teaches, for example, bending of the finger (for on-demand use) or with the help of a biased piston (for continuous use). On the vertical, or "Y" axis is the corresponding tissue pressure or pressure on the artery (and, accordingly, the sensor being used).

Various important aspects of the curve will now be described:

Curve 1-2 depicts how blood pressure would behave if outside pressure were applied on the artery when the artery is full of blood.

Curve 3-4 depicts how blood pressure would behave if outside pressure is applied on the artery when the artery is empty, i.e., has no blood in it.

Curve 1-A-D-4 curve indicates how pressure on the sensor would behave if blood pressure is always maintained at the diastolic (i.e., low) level. Note that segment A-D signifies emptying of the artery.

Curve 1-B-C-4 indicates how pressure on the sensor would behave if blood pressure is always maintained at the systolic (i.e., high) level.

There should generally be precise one-to-one dependence between the X and Y parameters except in the area of A-B-C-D, where we observe pressure fluctuations on the Y axis for any given X value. By way of illustration, $P_{S1}$, $P_{S2}$, and $P_{S3}$ depict three thresholds. As shown in FIG. 6, $P_{S1} < P_{dia}$ (diastolic pressure); $P_{dia} < P_{S2} < P_{sys}$ (systolic pressure); and $P_{S3} > P_{sys}$. For thresholds $P_{S1}$ and $P_{S3}$, corresponding $\partial_1$ and $\partial_3$ levels would have single, precise values (and could trigger an Off/On switch of the sensor). For $P_{S2}$, however, there exists a range of oscillations (between $\partial_2$ and $\partial_2'$) caused by blood pressure changes during the cardiac cycle. Due to these oscillations, the pressure on the sensor would change, from point M below the $P_{S2}$ threshold (sensor Off) to point K above the $P_{S2}$ threshold (sensor On). Accordingly, at any point within the $P_{dia}$-$P_{sys}$ range, pressure outside the artery always has a certain range that can be captured by an oscillometric sensor. Both diastolic and systolic blood pressure levels can therefore be identified. In fact, any threshold within $P_{dia}$-$P_{sys}$ range can also be identified, making so-called critical pressure sensors possible (as described herein).

Example 6

Figure 7:
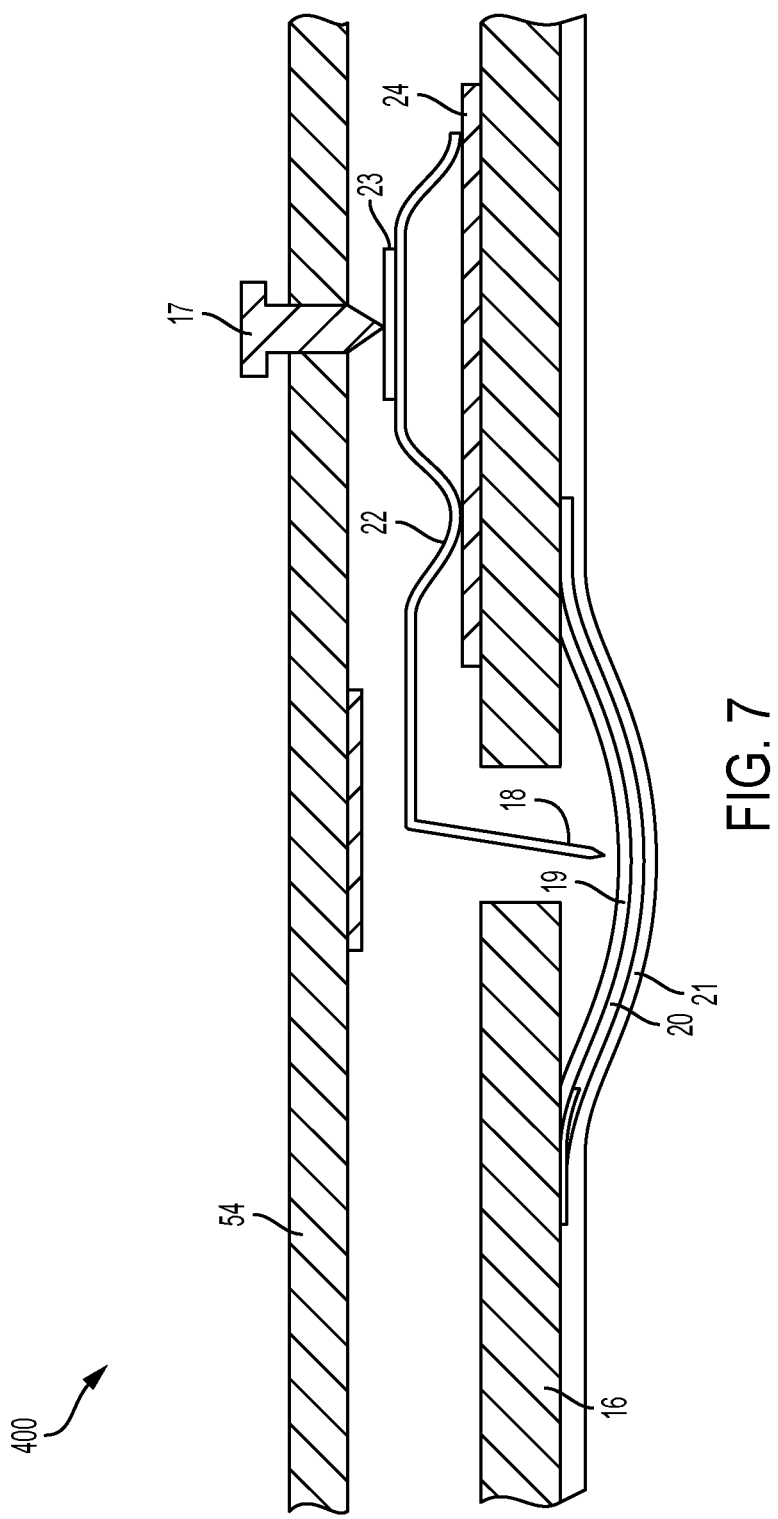
FIG. 7 is a sectional side view of an illustrative critical pressure sensor suitable for use in a pressure of blood monitoring device according to aspects of the present disclosure.

This example describes an illustrative critical sensor 400 suitable for use in BP monitoring devices as described in Examples 1-3; see FIG. 7.

Critical pressure sensor 400 may include any suitable sensor configured to switch between on and off when a critical (pre-specified) blood pressure level is detected. Accordingly, this type of sensor may be used to provide an alert to the patient. Referring back to FIG. 6, when outside the $P_{dia}$-$P_{sys}$ range (such as at $P_{S1}$ and $P_{S3}$), pressure applied on the sensor always has a precise value for any corresponding point on the X axis. However, at any point within the $P_{dia}$-$P_{sys}$ range, pressure outside the artery has a range that can be captured by an oscillometric sensor. In other words, a critical pressure sensor would turn On→Off→On as blood pressure fluctuates. Critical blood pressure devices can therefore be built that would alert patients when a certain pre-specified threshold falls within the $P_{dia}$-$P_{sys}$ range. In some examples, such a monitor may be able to accommodate both systolic and diastolic thresholds. In some examples, if pressure around the artery is stabilized by a biased piston (e.g., at level $P_{S2}$), the piston will be displaced between $\partial_2$ and $\partial_2'$ during the cardiac cycle. This movement can be detected by a movement sensor, thereby forming a continuous critical pressure monitor.

Turning now to FIG. 7, sensor 400 may include a top 54 and bottom 16 surface of cylindrical chamber 2. The top part may have a circular pressure scale (not shown) which has one hand that is attached to a control screw 17. The position of the hand (corresponding to a certain level on the pressure scale) determines a distance between electrical contact element 18 and electrical contact element 19. Element 18 may include the extension of a spring 22 that is shaped such that, as screw 17 is turned in one direction (e.g., clockwise), the distance between elements 18 and 19 increases. Spacing elements 18 and 19 farther apart increases a threshold for the sensor to turn on, because element 19, which is affected by pressure, has farther to travel before making the connection. Likewise, if screw 17 is turned in the other direction (e.g., counterclockwise), the threshold for the sensor is lowered. Element 19 may include a convex, curved spring leaf, and may have a finger-facing surface covered with dielectric layer 20 (e.g., Teflon) and an adhesive 21. When the adhesive side is pressed against the finger (e.g., by bending the finger), pressure builds in soft tissue 9 of the finger and thus around artery 7. The distance between elements 18 and 19 determines how much spring pressure must be overcome, and therefore the pressure level at which the sensor is turned on. The greater the distance, the greater the pressure would need to be to turn the sensor on. Additional dielectric layers 23 and 24 provide insulation for elements 18 and 19 when there is no contact between the two.

Referring back to FIG. 6, there will be a range of thresholds where pressure oscillations would turn the sensor from off to on and back for any pre-specified level between $P_{dia}$ and $P_{sys}$. This enables devices that would alert patients when their blood pressure exceeds or drops below a certain pre-specified or selected level.

Example 7

Figure 8:
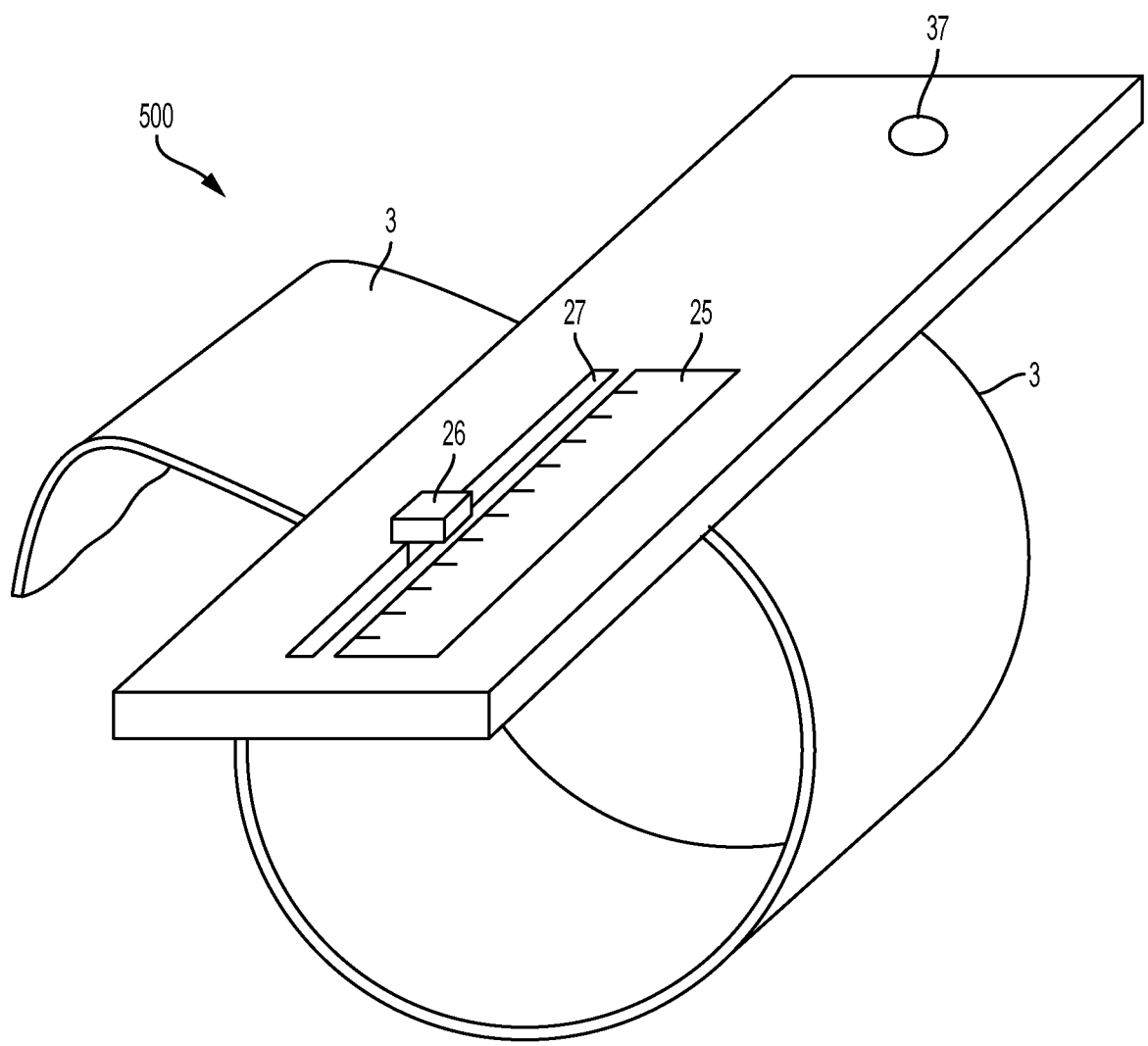
FIG. 8 is an isometric view of another illustrative critical pressure sensor suitable for use in a pressure of blood monitoring device according to aspects of the present disclosure.
Figure 9:
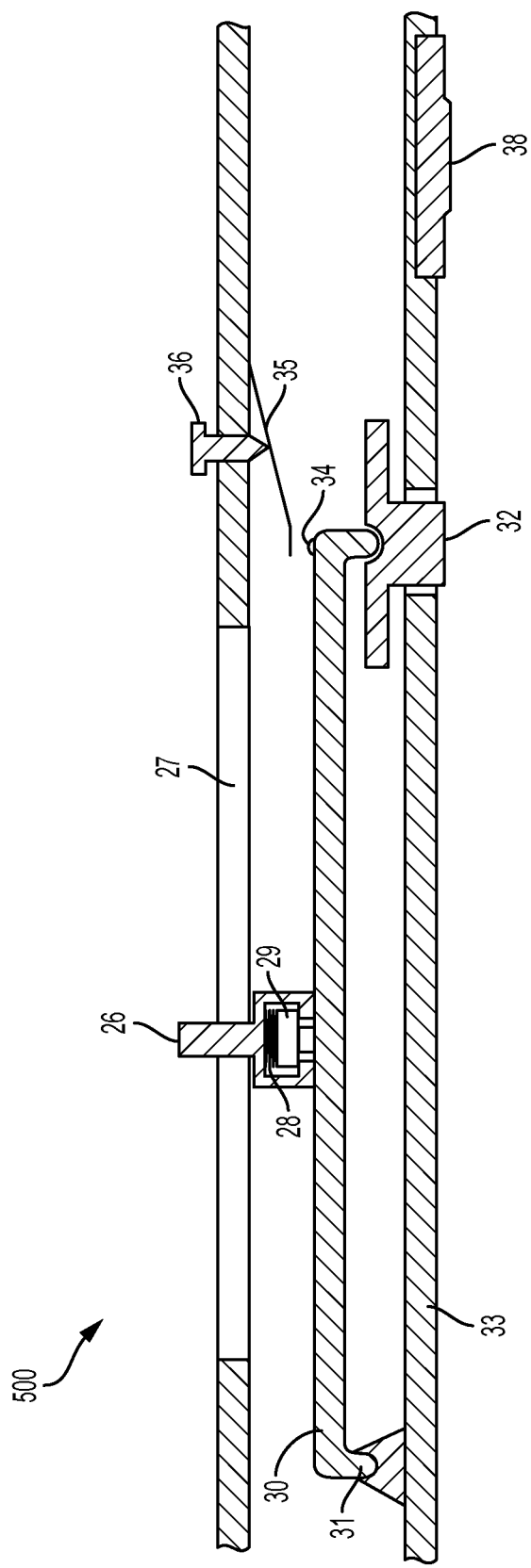
FIG. 9 is a sectional side view of the sensor of FIG. 8.

This example describes another illustrative critical sensor 500 suitable for use in BP monitoring devices as described in Examples 1-3; see FIGS. 8-9.

Sensor 500 may include a linear pressure scale 25. Thresholds are set with a runner 26 that slides along a channel 27. The runner has a spring 28 disposed within its cavity that presses on a button 29 that in turn presses on a crossbar 30. The crossbar rests and pivots on a bearing 31 at one end, and on a button 32 at the opposite end. Another surface of button 32 includes a specific surface area pressing on the finger, representing a part of the total pressure area of panel 33. Movement of the runner along channel 27 changes the location of a pressure point created by spring 28 and button 29, and thereby changes the amount of pressure applied on button 32 against panel 33.

When the panel is pressed against the finger (e.g., by bending the finger), button 32 is configured to detach from the panel and trigger an electric contact between elements 34 and 35 when the outside pressure created exceeds the pressure created by the ratio of pressure from the crossbar on the bottom to the surface area of the button against the finger. When elements 34 and 35 come in contact, an LED 37 may turn on, indicating that the pre-specified critical pressure level is reached. A position of element 35 may be adjusted with a screw 36 to ensure elements 34 and 35 are sufficiently close to each other.

In order for the patient to see whether the pre-specified critical pressure level is within the area of oscillations (between $P_{dia}$ and $P_{sys}$), the device may incorporate another sensor 38 that detects pulse pressure oscillations. Sensor 38 may require use of another LED. If the critical pressure sensor turns on while sensor 38 is able to detect oscillations (i.e., a pulse), then the pre-specified critical level lies within the $P_{dia}$ and $P_{sys}$ range. The converse is also true. Sensor 38 may include piezoelectric components, but may include any suitable mechanism sensitive to pulse pressure oscillations. When used with devices such as described in Example 6, sensor 38 should be located close to leaf spring sensor 19.

Example 8

Figure 10:
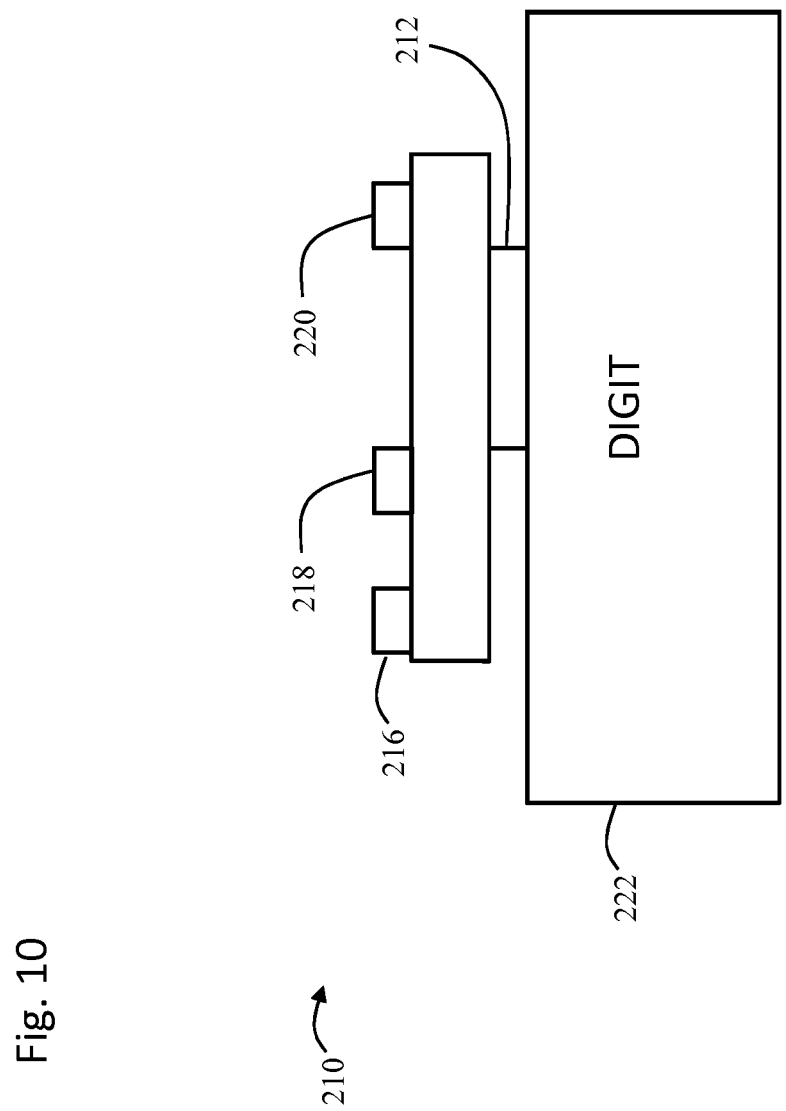
FIG. 10 is schematic diagram showing relationships between components of another illustrative pressure of blood monitoring device.

This example describes an illustrative digit-mounted BP monitoring device generally indicated at 210; see FIG. 10.

FIG. 10 is a schematic diagram showing relationships between various components that may be included in BP monitoring device 210. In this example, BP monitor 210 may include a sensor 212 which may be incorporated into a printed circuit board 214. The printed circuit board 214 may support other elements, such as a processor 216, an indicator 218, and a battery 220. BP monitor 210 may be configured to be applied to an area of a body, for example a digit 222, such as a human finger.

Sensor 212 may include one or more suitable sensors configured to sense and/or measure one or more desired physical or physiological characteristics when placed adjacent to, for example, digit 222 and convert the information into a useable format such as an electrical and/or digital signal. For example, sensor 212 may include a device sensitive to pressure, pulse, sound, light, motion, temperature, chemical composition or changes, electromagnetic fields, moisture, vibration, oscillation, and/or any combination of these. In some examples, sensor 212 may include an electronic sensor. In some examples, sensor 212 may include a mechanical sensor. In some examples, sensor 212 may include a selectable sensitivity feature.

Sensor 212 may be attached to the printed circuit board 214. Sensor 212 may be incorporated into printed circuit board 214, so that at least one component of sensor 212 is an inherent component of the printed circuit board itself.

The printed circuit board 214 may have a long axis aligned with the long axis of digit 222 and span the distance between opposite terminal condyles of a phalanx bone in the digit. The printed circuit board may be substantially the same size as or smaller than a credit card. The printed circuit board may provide physical support for sensor 212 and may be configured to maintain physical contact between sensor 212 and an area of the body, for example digit 222. The printed circuit board may comprise one or more components of sensor 212.

Processor 216 may include any suitable data processing device or controller (as further described below), and may be configured to respond to information provided by sensor 212. For example, processor 216 may be programmed or configured to respond to pressure above a certain setpoint by turning on an LED indicator 218 and/or displaying a textual or numeric value on a display indicator 218. Processor 216 may include aspects capable of receiving inputs and/or adjustments from a user through a user interface. For example, processor 216 may be connectable to another device having a graphical user interface and an input device through which various aspects and/or setpoints of BP monitor 210 may be selected and/or adjusted. In some examples, setpoints may be adjusted by mechanical interfaces on BP monitor 210 itself. In some examples, processor 216 may be excluded and an output of sensor 212 may directly control indicator 218.

Indicator 218 may include any suitable human-perceptible indicator configured to provide information related to the functioning of BP monitor 210. For example, indicator 218 may include one or more audible, visual, and/or tactile features. Indicator 218 may include a digital display, a light or LED, a speaker, a positional indicator, a color indicator, a pop-up button, a vibrating component, and/or the like, and/or any combination of these. In some examples, indicator 218 may be excluded from the device.

Battery 220 may provide power for processor 216, sensor 212, indicator 218, and/or any other components that require electrical power.

Example 9

Figure 11:
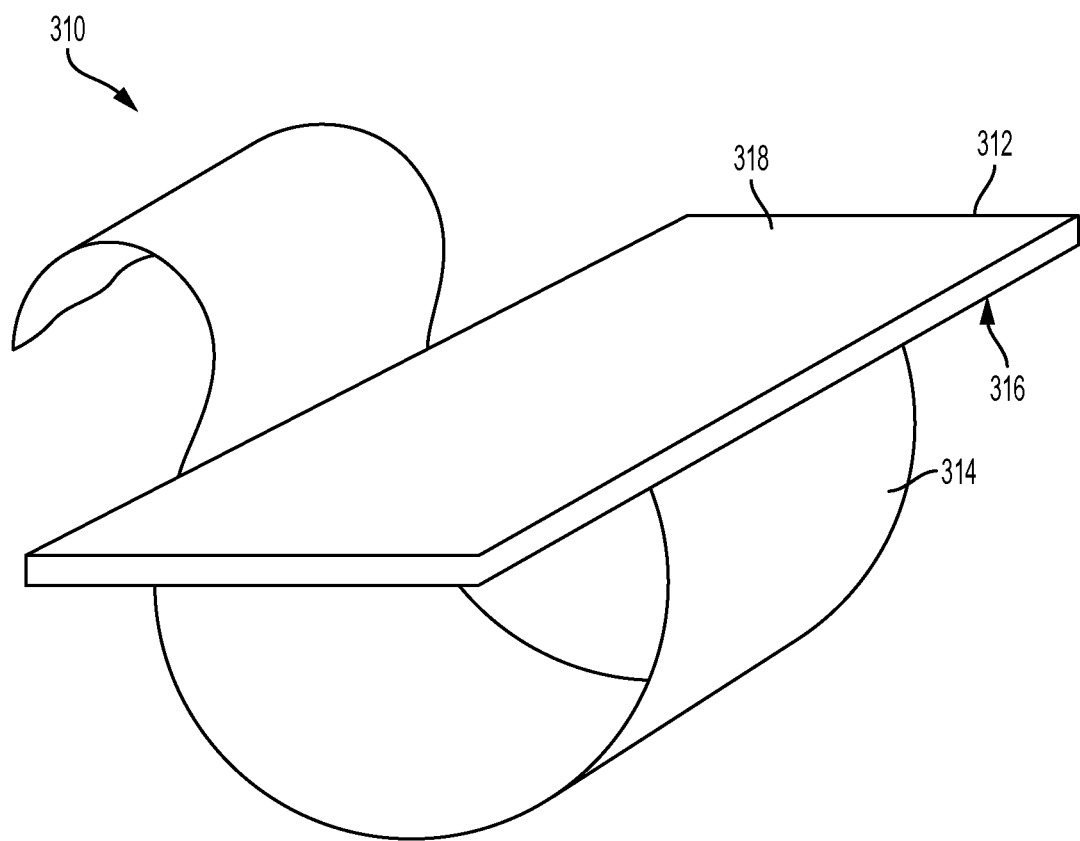
FIG. 11 is an isometric view of an illustrative pressure of blood monitoring device according to aspects of the present disclosure.
Figure 12:
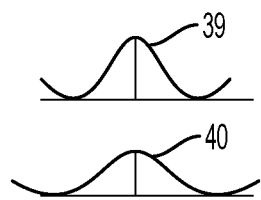
FIG. 12 is a sectional side view of an illustrative proportional sensor suitable for use in a pressure of blood monitoring device according to aspects of the present disclosure.
Figure 12:
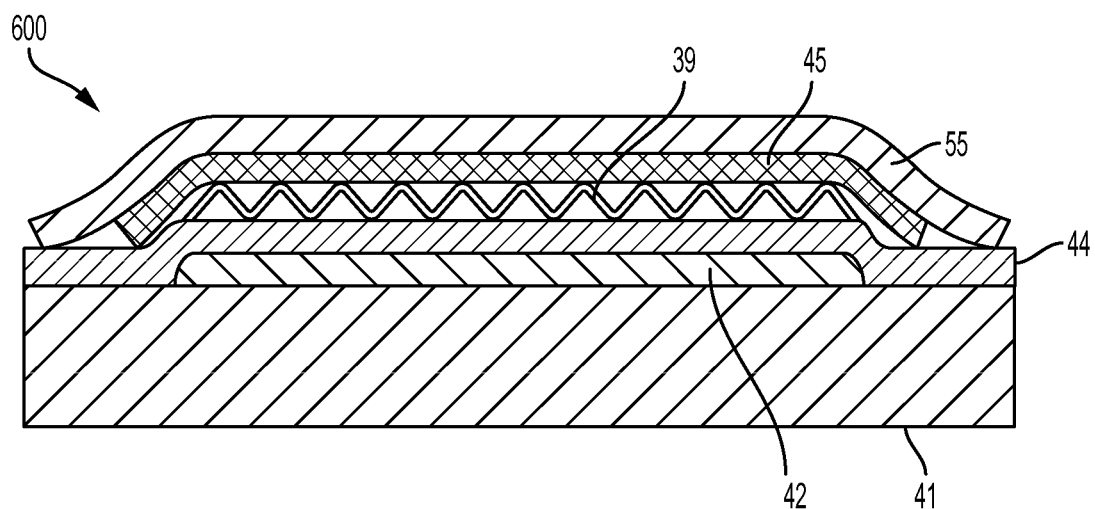
Figure 13:
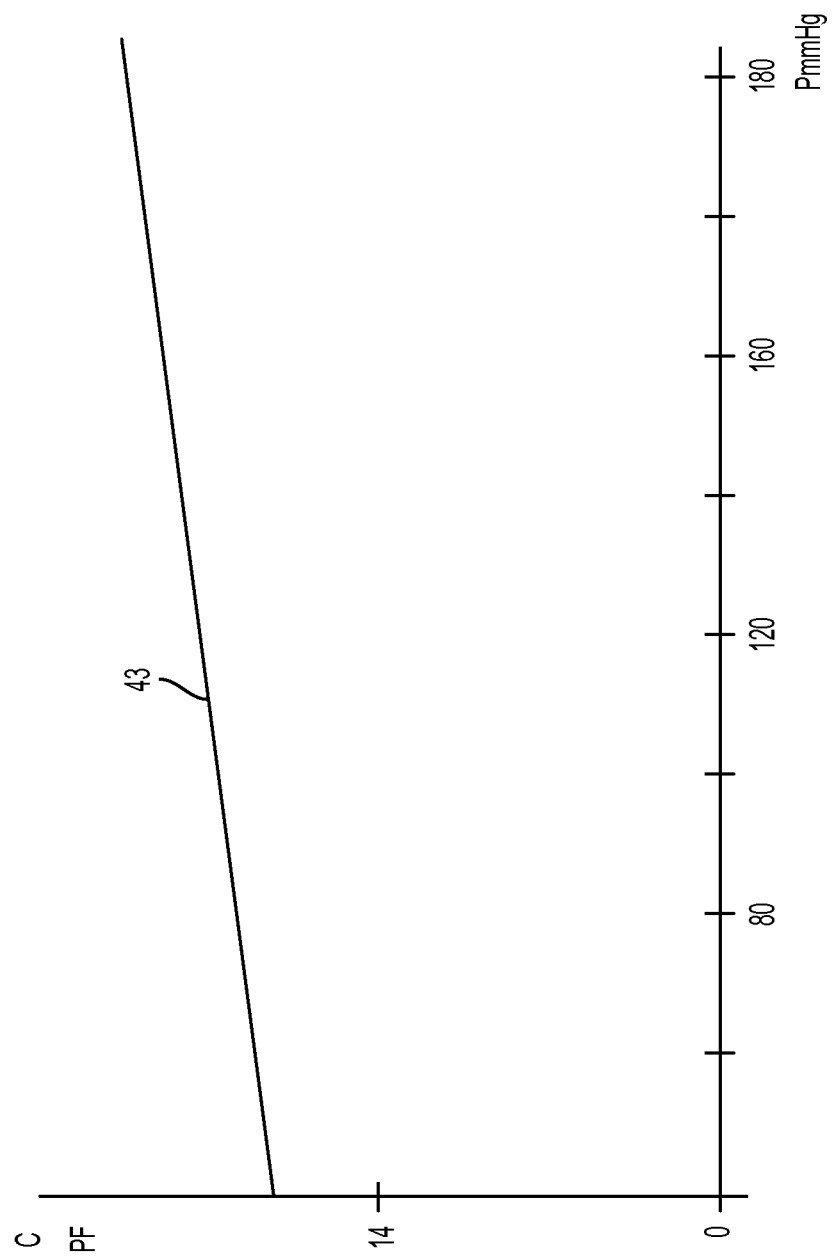
FIG. 13 is an exemplary calibration curve associated with the sensor of FIG. 12.

This example describes an illustrative BP monitoring device 310 including a printed circuit board, the device configured to be placed on the side of a finger; see FIGS. 11, 12, and 13.

FIG. 11 is a schematic isometric view of BP monitoring device 310. In this example, BP monitor 310 may include a printed circuit board 312. BP monitor 310 may include a strap 314 affixed to the panel at one end, and a lock mechanism (not shown) for the other end of the strap. Strap 314 may be any suitable strap or other attachment device configured to secure monitor 310 to a finger. Monitor 310 may be used on any appropriate body area, such as a finger, and may be used on an index finger. BP monitor 310 may include a proportional sensor on a first side 316 of the printed circuit board 312. The proportional sensor may be positioned on the first side 316 of the printed circuit board so that the proportional sensor is in physical contact with the finger when BP monitor 310 is secured to the body area. An example of a proportional sensor attached to a printed circuit board can be seen in FIG. 12.

As described in Example 8 above and as illustrated in FIG. 10, the printed circuit board 312 may support various components of BP monitor 310 on a second side 318 of the printed circuit board. A processor, display, and/or a battery may be connected to printed circuit board 312 on the second side 318.

FIG. 12 is a sectional side view of an illustrative proportional sensor 600 suitable for use in a blood pressure monitoring device. Sensor 600 may include a corrugated leaf spring 39 which flattens out when pressure is applied to sensor 600. FIG. 12 depicts leaf spring 39 in an uncompressed state proximate that same spring shown at 40 in a compressed or flattened out state. For example, leaf spring 39 may include a tempered stainless steel foil one half of one millimeter thick formed into a corrugated shape. The distance between adjacent peaks of the corrugation may be approximately 1 millimeter. Leaf spring 39 may be isolated from a conductive layer 42 by an insulating layer 44. Together, leaf spring 39, conductive layer 42, and insulating layer 44 may form a capacitor. As pressure is applied to sensor 600, leaf spring 39 may compress or flatten out, decreasing the effective distance between leaf spring 39 and conductive layer 42 and, in turn, increasing the capacitance of the capacitor. The layers of the capacitor may be configured so that the capacitance increases linearly with pressure, see FIG. 13. Sensor 600 may be said to be a "proportional sensor" in the sense that the capacitance may increase linearly with the applied pressure. Sensor 600 may be said to be a "capacitive sensor" in the sense that it may use a capacitor to measure applied pressure.

Sensor 600 may be supported on a base layer 41. Some or all of the base layer 41, the conductive layer 42, and the insulating layer 44 may be component layers of circuit board 312. The conductive layer 42 may be any layer of metallization comprising, for example, copper or gold and may have a thickness in a range of 1 to 10 microns. The insulating layer 44 may be any insulating layer and may have a thickness in a range of 10 to 20 microns.

There may be a first protective layer 45 disposed over leaf spring 39. The first protective layer may be Teflon tape with a thickness of approximately 50 microns. There may be a second protective layer 55 disposed over the first protective layer 45. The second protective layer may be adhesive Teflon tape with a thickness of approximately 70 microns. Either of the first or second protective layers may be omitted and there may be additional protective layers not shown in FIG. 12. One or both of the first and second protective layers may extend beyond the leaf spring 39 and one or both of the first and second protective layers may make contact with insulating layer 44. One or both the first and second protective layers may cover one or more of the components described herein and may be attached at any desired point to cover the one or more components.

Sensor 600 may be very thin. The total thickness of the conductive layer 42, the insulating layer 44, the leaf spring 39, the first protective layer, and the second protective layer may be as thin as approximately 100 microns. Such a thin sensor would not appreciably increase the thickness of the printed circuit board on which the sensor is mounted. Further, by incorporating sensor 600 into printed circuit board 312, the electric circuitry required to measure the capacitance of the capacitor may be built in to the printed circuit board.

FIG. 13 shows an illustrative calibration diagram associated with sensor 600. The layers of the capacitor may be configured so that the capacitance increases linearly with pressure. Curve 43 in FIG. 13 is an exemplary calibration curve that may be used with sensor 600. FIG. 13 depicts a graph of capacitance on the "y"-axis, measured in picofarads and pressure on the "x"-axis, measured in mmHg. The pressure is the pressure exerted on sensor 600 by the soft tissue in contact with sensor 600 and the capacitance is the capacitance of the capacitor comprised of the leaf spring 39, the conductive layer 42, and the insulating layer 44. The scales of the x and y axes are exemplary and not meant to be limiting in any way. The slope and y-intercept of curve 43 are also meant to be exemplary and not limiting in any way. Indeed, it is not required that curve 43 be strictly linear. All that is required of curve 43 to be an effective calibration curve is that curve 43 is a one-to-one function. Such a calibration curve can be created by applying known pressures to sensor 600 and measuring the corresponding capacitances. This calibration curve can then be stored and later used to determine the applied pressure for a given measured capacitance. If the correspondence between capacitance and pressure is one-to-one, such as with linear curve 43, then for every measured capacitance there will be exactly one indicated pressure.

Example 10

Figure 14:
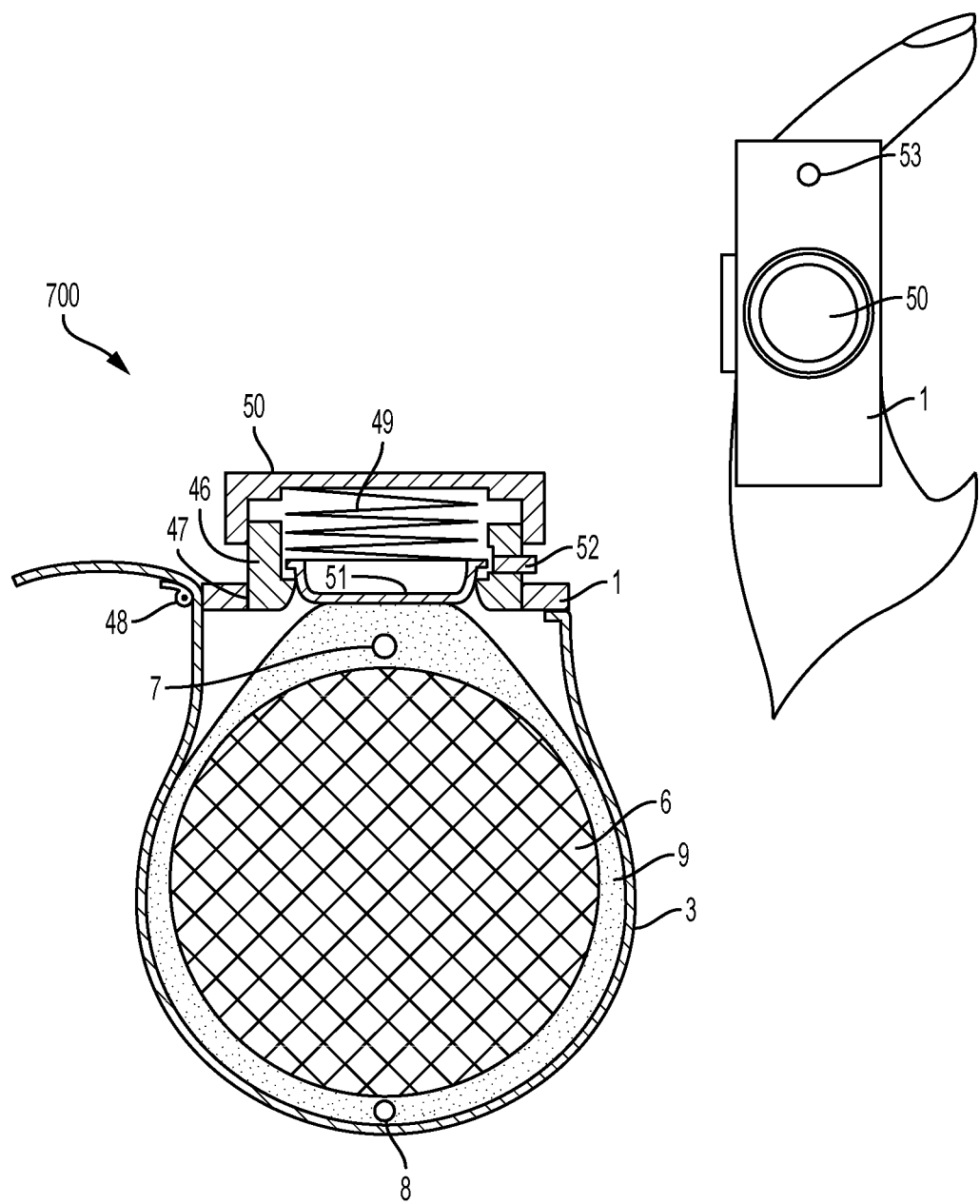
FIG. 14 is an illustrative continuous sensor suitable for use in a pressure of blood monitoring device according to aspects of the present disclosure.

This example describes an illustrative BP monitoring device having a continuous sensor 700; sensor 700 may also be suitable for use in BP monitoring devices as described in Examples 1-3; see FIG. 14.

FIG. 14 is a sectional, lateral view of sensor 700 on a finger. The base of a sensor insert 46 may be screwed into a central part of base panel 1 of the device via a threaded chamber 47 such that the base of the sensor comes in contact with the skin of the finger when tape or strap 3 is wrapped around the finger in a snug but comfortable fashion. A loose end of tape or strap 3 may be fixed with a lock mechanism 48 (e.g. a buckle). Inside sensor insert 46, a spring 49 may be contained from the top with a lid 50. The base of spring 49 pushes against a sensor insert 51, which in turn pushes against the surface of the finger. The spring should be sized such that the pressure it exerts when compressed stays roughly constant despite pressure changes created by finger movement.

Because the pressure applied by the insert on the skin cannot materially exceed the pressure created by the spring, a roughly constant level of pressure can be created. The base of insert 51 may contain a sensor 52 that tracks movement of sensor insert 51 and thereby detects the presence of oscillations. This sensor can be equipped with an LED 53, or other indicator, to alert the patient if blood pressure exceeds or drops below a pre-specified level. To facilitate changing the pre-specified level in this configuration, another sensor insert may be used, with a different spring. Alternatively, a different configuration is possible. For example, this device can be configured akin to the device in FIGS. 8-9, where button 32 is replaced with a piston with a large enough area, movement sensor 52 may be attached to element 35, and the design of the runner accommodates a larger angular range of motion for the crossbar 30.

Example 11

This example describes an illustrative BP monitoring device having a critical sensor, such as the ones illustrated in FIGS. 7-9, and associated methods.

A patient may specify a certain blood pressure level, such as by positioning a runner on a blood pressure scale. This level becomes a setpoint for the critical pressure sensor, which triggers an LED when outside pressure on the artery (e.g., from bending the finger) exceeds the setpoint. The patient then bends his or her finger gradually while crossing the point where the LED is lit. If the setpoint happens to be inside the $P_{dia}$-$P_{sys}$ range, the patient will observe oscillations resulting from the pressure pulse. If the setpoint lies outside of this range, the sensor will not register oscillations.

This type of BP monitoring device may be simple and inexpensive to make relative to other examples. It is also very reliable, due to its simplicity and low energy use. For example, the device may only use batteries during measurement and does not need to be switched off when not in use.

Example 12

This example describes an illustrative BP monitoring device having a critical sensor, such as the ones illustrated in FIGS. 7-9, and a pulse sensor, and associated methods.

As in Example 11, a patient may specify a certain blood pressure level, such as by positioning a runner on a blood pressure scale. Here, either diastolic or systolic levels can be set. This level becomes a set-point for the critical pressure sensor which triggers an indicator such as an LED when outside pressure on the artery (e.g., from bending the finger) exceeds the setpoint. This device may also have another sensor which detects pulse pressure oscillations, equipped with its own LED. When the patient bends the finger, pulse pressure is only sensed if within the $P_{dia}$-$P_{sys}$ range. If the critical pressure sensor LED turns on prior to the pulse sensor LED, the patient's diastolic blood pressure is above the pre-specified setpoint. If the critical pressure sensor LED turns on after the pulse sensor LED turns off, the patient's systolic pressure is below the pre-specified setpoint. If the critical pressure sensor LED turns on while the pulse sensor LED is still lit, the setpoint is within the $P_{dia}$-$P_{sys}$ range, informing the patient that blood pressure is either (a) at or above the pre-specified systolic level, and/or (b) at or below the pre-specified diastolic level, depending on which level was pre-specified.

This type of device may have advantages in that it does not require the user be trained in gradual finger bending in order to observe oscillations around set-points. The two types of devices may also be used in the same fashion if the user so prefers.

The type of device described in this example may include two sensors, and may require an amplifier and a power source for the oscillation sensor.

Example 13

This example describes an illustrative BP monitoring device having a proportional sensor, such as the one illustrated in FIGS. 11 and 12, and associated methods.

This device may function similarly to traditional blood pressure monitors in that it has one sensor which registers blood pressure oscillation equal to the mean blood pressure and associated pressure applied on the artery. The device may include a display and an electronic system which enables processing and memory of oscillation signals, and/or may be operatively connected to such a display and/or system. Unlike traditional monitors, this device does not use inflation to generate outside pressure. Rather, the user gradually bends his finger and the device generates $P_{dia}$, $P_{sys}$ and $P_{mean}$ values.

Example 14

This example describes an illustrative BP monitoring device having a critical sensor, such as the ones illustrated in FIGS. 7-9, and more specifically a continuous sensor as illustrated in FIG. 14, and associated methods.

This device is capable of continuous monitoring due to a feature that enables a constant pressure level on the artery regardless of the position of the finger (for low pressure levels) and constant pressure on the artery when the finger is bent in high blood pressure areas (but without fixation). The level of constant pressure is specified by the user, such as with a runner on a pressure scale of the device. The device is equipped with a sensor that detects pulse pressure oscillations in the area of the insert where constant pressure is applied.

In the areas of low blood pressure, when the set-point is below $P_{dia}$, this sensor detects no oscillations. However, as soon as blood pressure drops below the setpoint, oscillations are registered and the user can be alerted. In the areas of intermediate blood pressure, when the setpoint is in the $P_{dia}$-$P_{sys}$ range, oscillations will be registered. However, as soon as $P_{sys}$ drops below the pre-specified setpoint, oscillations cease and the user can be alerted. In areas of high blood pressure, the user will need to bend the finger since maintaining constant level at high levels is impractical. If the setpoint is above the $P_{sys}$ level, as long as $P_{sys}$ is below the setpoint the device detects no oscillations. However, as soon as $P_{sys}$ exceeds the set-point, oscillations can be registered and the user can be alerted. Note that this device does not require the user be skilled in gradual finger bending in order to observe oscillations around the set-point as the outside pressure cannot exceed the pre-specified level.

Example 15

This example describes a method for monitoring blood pressure, such as may be performed using one or more of the devices described above; see FIG. 15.

Figure 15:
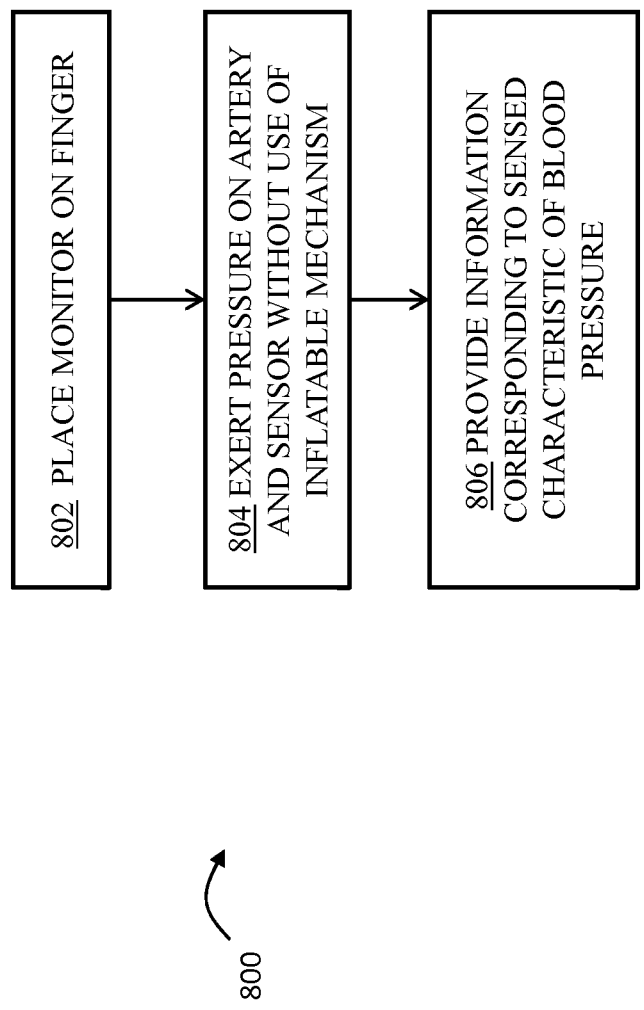
FIG. 15 is an illustrative method for monitoring pressure of blood suitable for use with pressure of blood monitoring devices according to aspects of the present disclosure.

FIG. 15 is a flowchart illustrating steps performed in an illustrative method, and may not recite the complete process or all steps of the process. FIG. 15 depicts multiple steps of a method, generally indicated at 800, which may be performed in conjunction with devices and methods according to aspects of the present disclosure. Although various steps of method 800 are described below and depicted in FIG. 15, the steps need not necessarily all be performed, and in some cases may be performed in a different order than the order shown.

At step 802, a BP monitor may be placed adjacent to an area of a body, such as a finger of a patient. For example, a BP monitor such as those described herein may be strapped or otherwise attached to a patient's finger. In some examples, the BP monitor may be attached to one side of the finger. In some examples, the BP monitor may be attached across a phalanx bone from side to side. In some examples, the BP monitor may be attached lengthwise to a finger, spanning opposing condyles of a phalanx bone.

At step 804, pressure may be exerted upon an artery, for example, in the finger as well as on a sensor in the BP monitor, without use of an inflatable cuff or other inflatable device. For example, the patient may bend the finger to cause soft tissue to fill a space under the sensor. For example, a biased piston may exert a preset amount of pressure on the soft tissue. In some examples, more than one sensor may be provided. Using a critical sensor, as described above, a patient may, for example, perform a quick, discrete check of blood pressure. This may be performed, for example, to determine if medication is needed. Using a "proportional" sensor, a patient may receive both exact systolic and diastolic pressure readings in one operation but faster and more conveniently than with traditional (inflatable cuff) monitors. In some examples, a continuous sensor may be used and a patient may monitor for low blood pressure. For example, this may be advantageous to predict lightheadedness or other symptoms.

Step 806 may include sensing oscillations when pressure is in the $P_{dia}$-$P_{sys}$ range. Step 806 may include sensing a pulse. Step 806 may include comparing a sensed pulse to a sensed pressure oscillation and/or absence of a pulse and/or absence of a pressure oscillation.

At step 806, an indication or other information corresponding to sensed blood pressure characteristics may be presented to the patient and/or any other user and/or a data processing system. For example, an LED light may be lit if blood pressure is sensed to be above a selected threshold. In some examples, a data processing system (see below) may receive data corresponding to the sensed blood pressure and/or a preselected threshold, and may be configured to respond in any suitable manner. For example, a data processing system may cause numerical, textual, and/or symbolic information corresponding to the BP characteristic(s) to appear on a display. For example, the LED light mentioned above may be driven by an output of the data processing system. For example, the data processing system may store data points for use in a time-based analysis such as a graph, table, or chart. For example, a message may be displayed and/or sound may be generated to alert the user to a potentially dangerous condition.

The data processing system may be incorporated into the BP monitor. The data processing system may be incorporated (at least in part) in another device or system. For example, a data processing system may be completely or partly disposed in a handheld device such as a smart phone, in a laptop or desktop computer, and/or in a tablet computer, and/or the like, and/or any combination of these. Information, also referred to as data, may be transferred from the sensor(s) to the indicator and/or data processing system in any suitable manner. For example, data may be transferred wirelessly, such as over wi-fi, Bluetooth, and/or Bluetooth Low Energy (BLE). In some examples, data may be transferred over a wired and/or optical connection, and/or the like, and/or any combination of these. In some examples, data may be processed by firmware and/or software such as a computer program or application. For example, data may be processed by a so-called "app" on a smart phone such as an iPhone, Android phone, and/or Windows phone, and/or the like.

This method may be performed in a hospital or medical environment. In some examples, the method may be performed in a home or mobile environment. A mobile use is facilitated by the reduced size and wearable nature of the device as compared to typical BP devices.

Example 16

This example describes a method for monitoring pressure of blood in an artery, such as may be performed using one or more of the devices described above, see FIG. 16.

Figure 16:
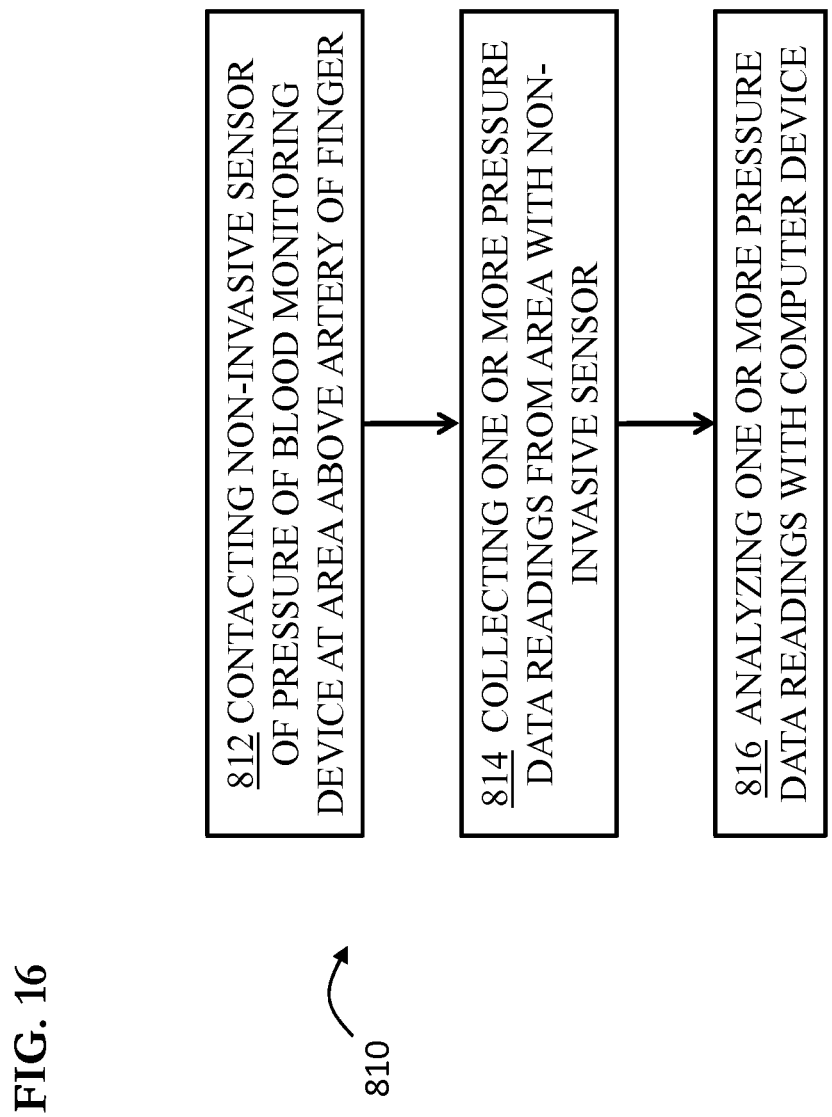
FIG. 16 is another illustrative method for monitoring pressure of blood suitable for use with pressure of blood monitoring devices according to aspects of the present disclosure.

FIG. 16 is a flow chart illustrating steps performed in an illustrative method, and may not recite the complete process or all steps of the process. FIG. 16 depicts multiple steps of a method, generally indicated at 810, which may be performed in conjunction with devices and methods according to aspects of the present disclosure. Although various steps of method 810 are described below and depicted in FIG. 16, the steps need not necessarily all be performed, and in some cases may be performed in a different order than the order shown.

At step 812, a non-invasive sensor of a blood pressure monitoring device may be contacted at an area above an artery of a finger. The sensor could be one or more of the sensors described herein, for example, sensors 400, 500, 600 or 700. The pressure monitoring device could be one or more of the monitoring devices described herein, for example, pressure monitoring devices 100, 200, 300, 210, or 310. The area above an artery of a finger may be an area on the side of a finger between a metacarpophalangeal (MCP) joint and a proximal inter-phalangeal joint (PIP).

At step 814, one or more pressure data readings from the area may be collected with the non-invasive sensor. The pressure data readings may be other than readings corresponding to an air pressure reading. Standard blood pressure monitors measure the pressure in a volume of air, however, the sensors disclosed herein all measure pressure of soft tissue under the skin, which is not an air pressure. Step 814 may occur after the contacting step 812 and after a pressure is exerted at the area on the sensor. The pressure exerted at the area may be caused by a bending of a finger. The bending may cause a higher pressure in the artery proximate the artery, relative to a lesser bending position. The bending may cause an injection of liquid proximate the area. This injection of liquid may improve the accuracy of any pressure data readings. The bending of the finger may be at a proximal inter-phalangeal (PIP) joint. The sensor may collect a plurality of pressure data readings continuously as the exerted pressure changes between a first pressure value and a second pressure value. The first pressure value may be either a minimum value or a maximum value. The second pressure value may be either a minimum value or a maximum value. A minimum value may be achieved when the finger is in a substantially unbent position. A maximum value may be achieved when the finger is in a bent or bending position. The first pressure value may be approximately 0 mmHg, approximately 300 mmHg, or any value in between 0 and 300 mmHg. For example, the first pressure value may be approximately 40 mmHg and the second pressure value may be approximately 180 mmHg. The sensor may collect pressure data readings continuously over a plurality of time intervals, every approximately 100 milliseconds, as the exerted pressure changes between the first and second pressure values. The pressure change may take place over approximately 30 seconds.

Figure 18:
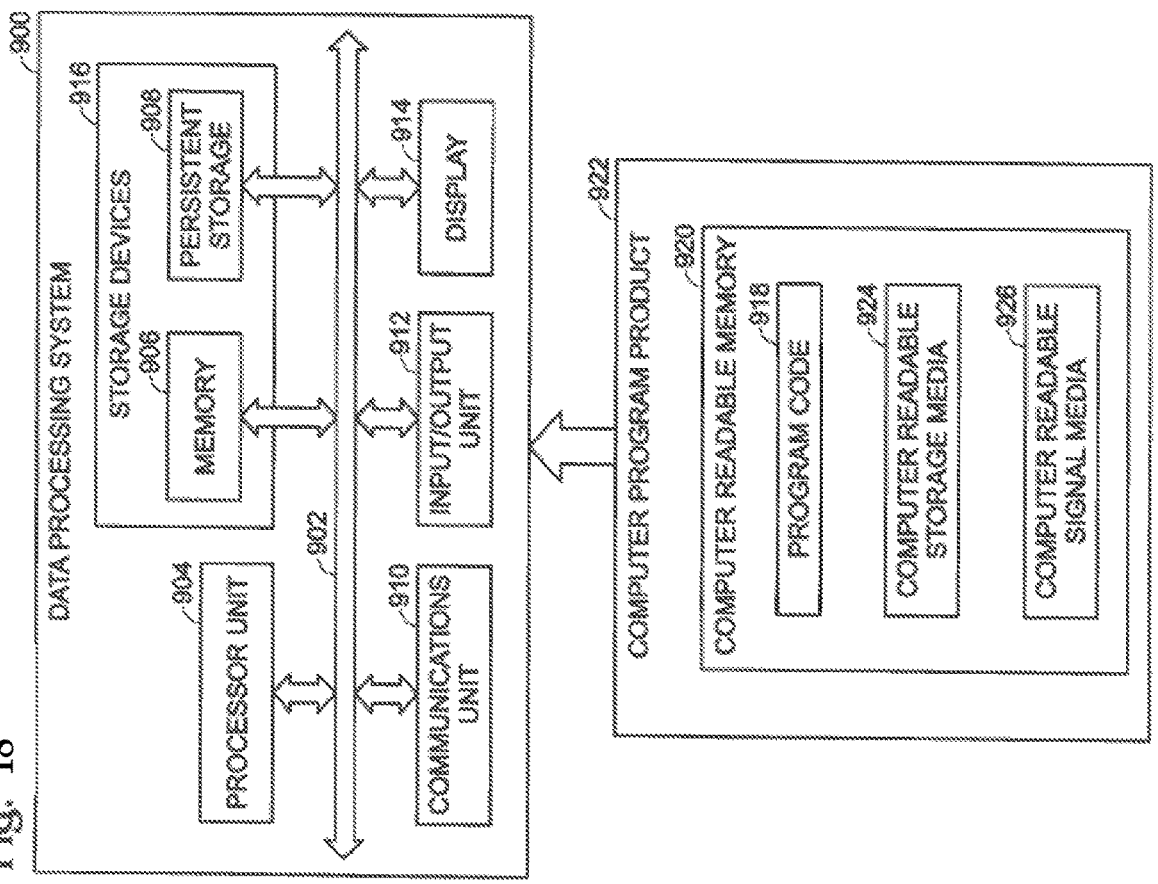
FIG. 18 is an illustrative data processing system suitable for use with pressure of blood monitoring devices and methods according to aspects of the present disclosure.

At step 816, one or more pressure data readings are analyzed with a computer device, for example that shown in FIG. 18. Analyzing the one or more pressure data readings may include generating at least one of a blood pressure reading and a heart pulse reading. Step 816 does not include analyzing any pressure data readings corresponding to an air pressure reading. Step 816 of analyzing the one or more pressure data readings may occur at the same time as step 814 of collecting the one or more pressure data readings. Both of steps 816 and 814 may occur over a range of time intervals. As discussed previously, the pressure data readings may be collected over an amount of time up to approximately 30 seconds. Step 816 of analyzing the pressure data readings could occur during and after that same amount of time. For example, one or more sensors may be configured to continuously monitor the area and may begin automatically collecting at least one reading after detecting with the non-invasive sensor a change in pressure at the area from a zero mmHg state to a non-zero mmHg state. This change may be in response to a bending of the finger. That is, as the computing device analyzes the pressure data readings and registers a change in pressure from a zero mmHg state, the sensor may automatically begin collecting at least one pressure data reading. The sensor may be configured to continuously monitor the area when the finger is in a position where the exerted force is approximately zero mmHg.

Method 810 may further include receiving at least one of the blood pressure reading and the heart pulse reading generated based on the one or more pressure data readings analyzed by the computer system.

Method 810 may further include attaching the pressure of blood monitoring device to a finger. The pressure of blood monitoring device may be part of a ring system that includes a printed circuit board coupled to the non-invasive sensor, see for example FIGS. 10-12.

Method 810 may further include measuring changes in capacitance in response to changes in pressure to generate the one or more pressure data readings as discussed in relation to FIGS. 12 and 13.

Example 17

This example describes a method for monitoring pressure of blood in an artery, such as may be performed using one or more of the devices described above, see FIG. 17.

Figure 17:
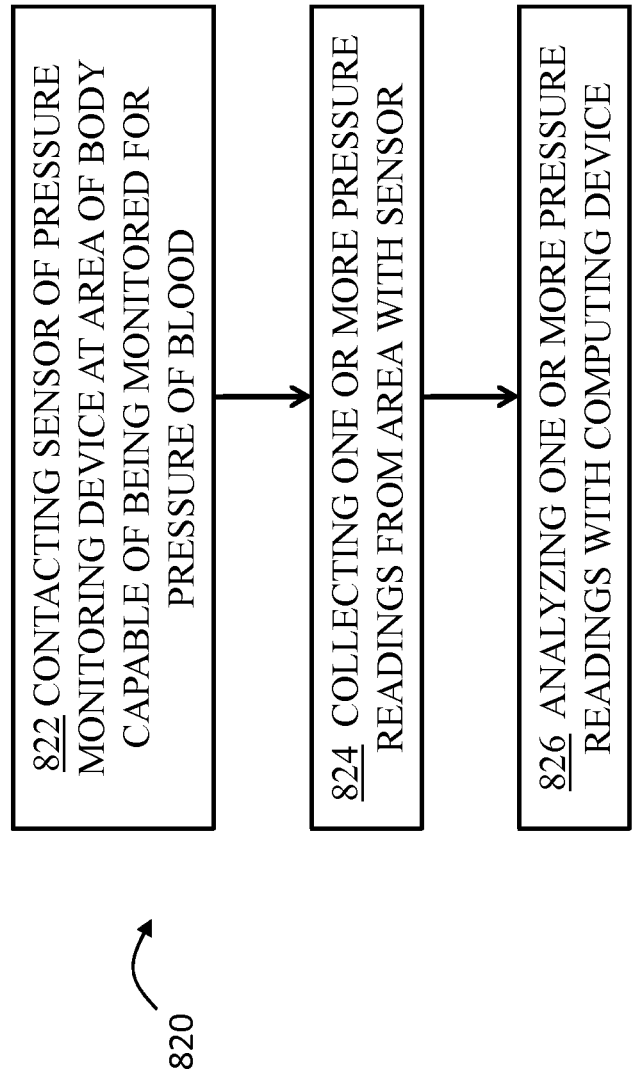
FIG. 17 is another illustrative method for monitoring pressure of blood suitable for use with pressure of blood monitoring devices according to aspects of the present disclosure.

FIG. 17 is a flow chart illustrating steps performed in an illustrative method, and may not recite the complete process or all steps of the process. FIG. 17 depicts multiple steps of a method, generally indicated at 820, which may be performed in conjunction with devices and methods according to aspects of the present disclosure. Although various steps of method 820 are described below and depicted in FIG. 17, the steps need not necessarily all be performed, and in some cases may be performed in a different order than the order shown.

At step 822, a sensor of a pressure monitoring device is contacted with an area of a body capable of being monitored for pressure of blood. The sensor could be one or more of the sensors described herein, for example, sensors 400, 500, 600 or 700. The pressure monitoring device could be one or more of the monitoring devices described herein, for example, pressure monitoring devices 100, 200, 300, 210, or 310. The area of the body capable of being monitored for blood pressure readings may be an area above an artery of a finger. The area above an artery of a finger may be an area on the side of a finger between a metacarpophalangeal (MCP) joint and a proximal inter-phalangeal joint (PIP).

At step 824, one or more pressure readings from the area may be collected with the sensor. For example, the capacitive sensor 600 may be used to collect one or more pressure readings. The one or more pressure readings may be collected after the contacting step 822. Step 824 of collecting pressure readings may be after a pressure is exerted at the area on the sensor. The sensor may collect a plurality of pressure data readings continuously as the exerted pressure changes between a first pressure value and a second pressure value. The first pressure value may be either a minimum value or a maximum value. The second pressure value may be either a minimum value or a maximum value. The first pressure value may be approximately 0 mmHg, approximately 300 mmHg, or any value in between 0 and 300 mmHg. For example, the first pressure value may be approximately 40 mmHg and the second pressure value may be approximately 180 mmHg. The sensor may collect pressure data readings continuously over a plurality of time intervals, every approximately 100 milliseconds, as the exerted pressure changes between the first and second pressure values. The pressure change may take place over approximately 30 seconds. The sensor may be configured to automatically collect a plurality of readings as the exerted pressure changes from the first pressure value to the second pressure value. Step 824 of collecting one or more pressure of blood readings with a sensor may occur without data generated from an air inflatable element. Indeed, all sensors disclosed herein and all blood pressure monitoring devices disclosed herein are capable of collecting pressure readings without an air inflatable element, for example, an air inflatable cuff. Instead of using an air inflatable element to change the pressure exerted at the area where pressure data readings are to be collected, the sensors disclosed herein measure pressures exerted at the area of the body that are caused by a bending of the finger.

At step 826, one or more pressure readings are analyzed with a computing device, for example see FIG. 18. Analyzing the one or more pressure data readings may include generating one or more health data readings based on the analysis of the one or more pressure data readings. The one or more pressure data readings may be analyzed to generate a blood pressure reading as the health data reading. The computing device may be remote or coupled to the sensor.

Method 820 may further include measuring an oscillation of pressure of blood readings over time intervals, see step 824, of the collected plurality of pressure readings to generate a heart pulse rate as the health data reading. Step 826 of analyzing the one or more pressure data readings may occur at the same time as step 824 of collecting the one or more pressure data readings. Both of steps 826 and 824 may occur over a range of time intervals. As discussed previously, the pressure data readings may be collected over an amount of time up to approximately 20 or 30 seconds, or any other time. Step 826 of analyzing the pressure data readings could occur during and after that same amount of time. For example, one or more sensors may be configured to continuously monitor the area and may begin automatically collecting at least one reading after detecting with the capacitive sensor a change in pressure at the area from a zero mmHg state to a non-zero mmHg state. That is, as the computing device analyzes the pressure data readings and registers a change in pressure from a zero mmHg state, the sensor may automatically begin collecting at least one pressure data reading.

Method 820 may further include analyzing a change in capacitance of the capacitive sensor to generate the one or more pressure data readings. The capacitance of the capacitive sensor may change due to a change in configuration between conductive materials of the capacitive sensor. For example, in the capacitive sensor shown in FIG. 12, the configuration of conductive materials 39 and 42 may change as pressure is applied to the sensor and the conductive materials become closer together.

Method 820 may further include providing a pressure monitoring device that includes the capacitive sensor, the capacitive sensor being configured to be in contact with the area of skin above an artery. The capacitive sensor may include a conductive element disposed on a bottom side adjacent a printed circuit board, such as conductive layer 42 shown in FIG. 12. The capacitive sensor may include a resilient member, such as leaf spring 39 shown in FIG. 12. The capacitive sensor may include an insulation layer separating the conductive element from the resilient member, such as insulating layer 44 shown in FIG. 12, and an adhesive layer covering the resilient member, such as the first or second protective layers 45 and 55 shown in FIG. 12. The capacitive sensor may be configured to collect one or more pressure of blood data readings while in contact with the area. Providing the pressure monitoring device may include a data processing device, in communication with the capacitive sensor, configured to analyze data readings produced by the sensor, the data processing device including a processor, a memory, and a set of instructions stored in the memory and executed by the processor to determine whether the information provided by the sensor meets selected criteria, and providing an alert to a user if the information meets the criteria.

Method 820 may further include providing the pressure monitoring device with an attachment portion that houses the sensor, see for example, FIG. 11. The pressure exerted on the sensor from the finger may be caused by the bending of the finger.

Example 18

This example describes a data processing system 900 in accordance with aspects of the present disclosure. In this example, data processing system 900 is an illustrative data processing system for implementing methods, measurement systems, and/or data handling portions of the devices and methods described above and shown in FIGS. 1-13; See FIG. 18.

In this illustrative example, data processing system 900 includes communications framework 902. Communications framework 902 provides communications between processor unit 904, memory 906, persistent storage 908, communications unit 910, input/output (I/O) unit 912, and display 914. Memory 906, persistent storage 908, communications unit 910, input/output (I/O) unit 912, and display 914 are examples of resources accessible by processor unit 904 via communications framework 902.

Processor unit 904 serves to run instructions for software that may be loaded into memory 906. Processor unit 904 may be a number of processors, a multi-processor core, or some other type of processor, depending on the particular implementation. Further, processor unit 904 may be implemented using a number of heterogeneous processor systems in which a main processor is present with secondary processors on a single chip. As another illustrative example, processor unit 904 may be a symmetric multi-processor system containing multiple processors of the same type.

Memory 906 and persistent storage 908 are examples of storage devices 916. A storage device is any piece of hardware that is capable of storing information, such as, for example, without limitation, data, program code in functional form, and other suitable information either on a temporary basis or a permanent basis.

Storage devices 916 also may be referred to as computer readable storage devices in these examples. Memory 906, in these examples, may be, for example, a random access memory or any other suitable volatile or non-volatile storage device. Persistent storage 908 may take various forms, depending on the particular implementation.

For example, persistent storage 908 may contain one or more components or devices. For example, persistent storage 908 may be a hard drive, a flash memory, a rewritable optical disk, a rewritable magnetic tape, or some combination of the above. The media used by persistent storage 908 also may be removable. For example, a removable hard drive may be used for persistent storage 908.

Communications unit 910, in these examples, provides for communications with other data processing systems or devices. In these examples, communications unit 910 is a network interface card. Communications unit 910 may provide communications through the use of either or both physical and wireless communications links.

Input/output (I/O) unit 912 allows for input and output of data with other devices that may be connected to data processing system 900. For example, input/output (I/O) unit 912 may provide a connection for user input through a keyboard, a mouse, and/or some other suitable input device. Further, input/output (I/O) unit 912 may send output to a printer. Display 914 provides a mechanism to display information to a user.

Instructions for the operating system, applications, and/or programs may be located in storage devices 916, which are in communication with processor unit 904 through communications framework 902. In these illustrative examples, the instructions are in a functional form on persistent storage 908. These instructions may be loaded into memory 906 for execution by processor unit 904. The processes of the different embodiments may be performed by processor unit 904 using computer-implemented instructions, which may be located in a memory, such as memory 906.

These instructions are referred to as program instructions, program code, computer usable program code, or computer readable program code that may be read and executed by a processor in processor unit 904. The program code in the different embodiments may be embodied on different physical or computer readable storage media, such as memory 906 or persistent storage 908.

Program code 918 is located in a functional form on computer readable media 920 that is selectively removable and may be loaded onto or transferred to data processing system 900 for execution by processor unit 904. Program code 918 and computer readable media 920 form computer program product 922 in these examples. In one example, computer readable media 920 may be computer readable storage media 924 or computer readable signal media 926.

Computer readable storage media 924 may include, for example, an optical or magnetic disk that is inserted or placed into a drive or other device that is part of persistent storage 908 for transfer onto a storage device, such as a hard drive, that is part of persistent storage 908. Computer readable storage media 924 also may take the form of a persistent storage, such as a hard drive, a thumb drive, or a flash memory, that is connected to data processing system 900. In some instances, computer readable storage media 924 may not be removable from data processing system 900.

In these examples, computer readable storage media 924 is a physical or tangible storage device used to store program code 918 rather than a medium that propagates or transmits program code 918. Computer readable storage media 924 is also referred to as a computer readable tangible storage device or a computer readable physical storage device. In other words, computer readable storage media 924 is a media that can be touched by a person.

Alternatively, program code 918 may be transferred to data processing system 900 using computer readable signal media 926. Computer readable signal media 926 may be, for example, a propagated data signal containing program code 918. For example, computer readable signal media 926 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 918 may be downloaded over a network to persistent storage 908 from another device or data processing system through computer readable signal media 926 for use within data processing system 900. For instance, program code stored in a computer readable storage medium in a server data processing system may be downloaded over a network from the server to data processing system 900. The data processing system providing program code 918 may be a server computer, a client computer, or some other device capable of storing and transmitting program code 918.

The different components illustrated for data processing system 900 are not meant to provide architectural limitations to the manner in which different embodiments may be implemented. The different illustrative embodiments may be implemented in a data processing system including components in addition to and/or in place of those illustrated for data processing system 900. Other components shown in FIG. 9 can be varied from the illustrative examples shown. The different embodiments may be implemented using any hardware device or system capable of running program code. As one example, data processing system 900 may include organic components integrated with inorganic components and/or may be comprised entirely of organic components excluding a human being. For example, a storage device may be comprised of an organic semiconductor.

In another illustrative example, processor unit 904 may take the form of a hardware unit that has circuits that are manufactured or configured for a particular use. This type of hardware may perform operations without needing program code to be loaded into a memory from a storage device to be configured to perform the operations.

For example, when processor unit 904 takes the form of a hardware unit, processor unit 904 may be a circuit system, an application specific integrated circuit (ASTC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 918 may be omitted, because the processes for the different embodiments are implemented in a hardware unit.

In still another illustrative example, processor unit 904 may be implemented using a combination of processors found in computers and hardware units. Processor unit 904 may have a number of hardware units and a number of processors that are configured to run program code 918. With this depicted example, some of the processes may be implemented in the number of hardware units, while other processes may be implemented in the number of processors.

In another example, a bus system may be used to implement communications framework 902 and may be comprised of one or more buses, such as a system bus or an input/output bus. Of course, the bus system may be implemented using any suitable type of architecture that provides for a transfer of data between different components or devices attached to the bus system.

Additionally, communications unit 910 may include a number of devices that transmit data, receive data, or both transmit and receive data. Communications unit 910 may be, for example, a modem or a network adapter, two network adapters, or some combination thereof. Further, a memory may be, for example, memory 906, or a cache, such as that found in an interface and memory controller hub that may be present in communications framework 902.

The flowcharts and block diagrams described herein illustrate the architecture, functionality, and operation of possible implementations of systems, methods, and computer program products according to various illustrative embodiments. In this regard, each block in the flowcharts or block diagrams may represent a module, segment, or portion of code, which comprises one or more executable instructions for implementing the specified logical function or functions. It should also be noted that, in some alternative implementations, the functions noted in a block may occur out of the order noted in the drawings. For example, the functions of two blocks shown in succession may be executed substantially concurrently, or the functions of the blocks may sometimes be executed in the reverse order, depending upon the functionality involved.

Numbered Paragraphs

This section describes additional aspects and features of pressure monitoring devices and methods, presented without limitation as a series of numbered paragraphs. Each of these paragraphs can be combined with one or more other paragraphs, and/or with disclosure from elsewhere in this application, including the materials incorporated by reference, if any, in any suitable manner. Some of the paragraphs below expressly refer to and further limit other paragraphs, providing without limitation examples of some of the suitable combinations.

A0. An apparatus for monitoring blood pressure, comprising:

a brace portion configured to span an anatomical feature of a human finger;

a sensor mount portion operatively connected to the brace portion such that the sensor mount portion is disposed over a target portion of soft tissue of the human finger when the brace portion spans the anatomical feature;

a sensor operatively connected to the sensor mount such that the sensor is adjacent to the target portion of soft tissue when the brace portion spans the anatomical feature;

an attachment portion operatively connected to the brace portion and configured to secure the apparatus to the finger with the brace portion spanning the anatomical feature.

A1. The apparatus of paragraph A0, wherein the anatomical feature is a phalanx bone and the brace portion spans a length of the phalanx bone.

A2. The apparatus of paragraph A0, wherein the sensor mount portion is centered in the brace portion.

A3. The apparatus of paragraph A0, wherein the sensor is configured to sense a parameter associated with blood pressure.

A4. The apparatus of paragraph A3, wherein the sensor is an oscillometric sensor.

A5. The apparatus of paragraph A0, wherein the attachment portion and brace are configured such that bending the finger with the device attached causes pressure to be exerted on an artery in the finger.

A6. The apparatus of paragraph A5, wherein the artery is a radial artery.

A7. The apparatus of paragraph A0, wherein the sensor is a critical pressure sensor.

A8. The apparatus of paragraph A7, wherein the sensor has a selectable setpoint.

A9. The apparatus of paragraph A0, wherein the sensor is a proportional sensor.

A10. The apparatus of paragraph A9, wherein the sensor includes a corrugated leaf spring deformable by pressure.

A10b. The apparatus of claim A10, wherein the proportional sensor measured changes in capacitance in response to changes in pressure.

A10c. The apparatus of claim A10, wherein the corrugated leaf spring forms a component of a capacitor.

A11. The apparatus of paragraph A0, wherein the sensor is a continuous sensor.

A12. The apparatus of paragraph A11, wherein the sensor is biased to apply a selected amount of pressure on the target soft tissue.

A13. The apparatus of paragraph A0, further including an indicator in communication with the sensor, the indicator providing a signal when sensed blood pressure meets a selected criterion.

A14. The apparatus of any other paragraph, further including a data processing system in communication with the sensor.

B0. A method for monitoring blood pressure, the method including:

attaching a blood pressure monitor to a finger of a patient;

exerting pressure on an artery in the finger without using an inflatable mechanism; and providing information corresponding to a sensed characteristic of the blood pressure.

B1. The method of paragraph B0, wherein attaching the blood pressure monitor includes strapping a blood pressure monitor to a side of the finger.

B2. The method of paragraph B0, wherein attaching the blood pressure monitor includes attaching a monitor having a flat panel and a strap, the flat panel having a void under an attached sensor, the void being placed over a portion of soft tissue on the finger.

B3. The method of paragraph B0, wherein exerting pressure includes bending the finger.

B3b. The method of paragraph B3, wherein the pressure has a first value of 0 mmHg when the finger is in a straight position and a second value of 300 mmHg when the finger is in a bent position.

B4. The method of paragraph B0, wherein exerting pressure includes exerting a predetermined amount of pressure using a biased sensor attached to the monitor.

B5. The method of paragraph B0, wherein providing information includes turning on a light.

B6. The method of paragraph B0, wherein providing information includes sensing an oscillometric characteristic of the finger.

B7. The method of paragraph B0, wherein providing information includes analyzing data from a sensor using a data processing system.

B8. The method of paragraph B0, further including continuously monitoring the blood pressure of the patient using a biased sensor attached to the monitor and in contact with soft tissue of the finger.

C0. A blood pressure monitor system comprising:
a blood pressure monitoring device having a rigid brace portion configured to span a phalanx bone of a human finger, a sensor operatively connected to the brace portion, and an attachment strap for securing the device to a finger; and
a data processing device for analyzing information provided by the sensor, the data processing device including a processor, a memory, and a set of instructions stored in the memory and executed by the processor to (a) determine whether the information provided by the sensor meets selected criteria, and (b) providing an alert to a user if the information meets the criteria.

C1. The system of paragraph C0, wherein the blood pressure monitoring device is configured to create pressure on an artery in the finger when a user bends the finger.

C2. The system of paragraph C0, wherein the instructions further include steps for storing historical data related to blood pressure.

D1. A method for monitoring pressure of blood in an artery, comprising:
contacting a capacitive sensor of a pressure monitoring device at an area of a body capable of being monitored for pressure of blood readings,
collecting with the capacitive sensor one or more pressure data readings from the area after the contacting and after a pressure is exerted at the area on the sensor; and
analyzing with a computing device the one or more pressure data readings to generate one or more health data readings based on an analysis of the one or more pressure data readings.

D2. The method of paragraph D1, further comprising collecting a plurality of pressure data readings continuously as the exerted pressure changes between 0 millimeters of mercury (mmHg) and 300 mmHg.

D3. The method of paragraph D2, further comprising continuously collecting readings over a plurality of time intervals as the pressure changes between zero mmHg and 300 mmHg.

D4. The method of paragraph D3, further comprising collecting pressure data readings at time intervals every approximately 100 milliseconds.

D5. The method of paragraph D2, wherein changing the exerted pressure continuously between zero mmHg and 300 mmHg occurs over approximately 30 seconds.

D6. The method of paragraph D2, further comprising analyzing the plurality of pressure readings to generate a blood pressure reading as the health data reading.

D7. The method of paragraph D2, further comprising measuring an oscillation of pressure of blood readings over time intervals of the collected plurality of pressure readings to generate a heart pulse rate as the health data reading.

D8. The method of paragraph D1, further comprising automatically collecting a plurality of readings continuously as the exerted pressure changes between zero millimeters mercury (mmHg) and 300 mmHg.

D9. The method of paragraph D1, further comprising
continuous monitoring by the sensor of the area, and
automatically collecting at least one reading after detecting with the capacitive sensor a change in pressure at the area from a zero mmHg state to a non-zero mmHG state.

D10. The method of paragraph D1, further comprising analyzing a change in capacitance of the capacitive sensor to generate the one or more pressure data readings.

D11. The method of paragraph D10, wherein analyzing a change in capacitance includes measuring a change in a configuration between conductive materials of the capacitive sensor.

D12. The method of paragraph D10, wherein measuring the one or more pressure of blood readings occurs without data generated from an air inflatable element.

D13. The method of paragraph D1, wherein contacting a capacitive sensor of a blood pressure monitoring device at an area of a body capable of being monitored for pressure of blood readings includes contacting the area above an artery of a finger.

D14. The method of paragraph D13, wherein the pressure exerted at the area is caused by a bending of the finger.

D15. The method of paragraph D13, wherein the pressure exerted at the area is caused by the finger bent at a proximal inter-phalangeal (PIP) joint.

D16. The method of paragraph D13, further comprising collecting at continuous time intervals one or more pressure of blood readings while the finger is bending from an unbent position to a bent position.

D17. The method of paragraph D13, further comprising collecting at continuous time intervals one or more pressure of blood readings while the finger is bending from a bent position to another bending or an unbent position.

D18. The method of paragraph D13, further comprising automatically activating the sensor to collect one or more pressure of blood readings in response to a bending of the finger.

D19. The method of paragraph D1, further comprising continuously monitoring with the sensor the area when the finger is in a position where the exerted force is zero mmHg.

D20. The method of paragraph D1, wherein contacting a capacitive sensor of a blood pressure monitoring device at an area of a body capable of being monitored for pressure of blood readings includes contacting the area above an artery on a side of a finger between a metacarpophalangeal (MCP) joint and a proximal inter-phalangeal joint (PIP) joint.

D21. The method of paragraph D1, further comprising sending data from the monitoring device to a computer system, the data including the one or more pressure of blood readings.

D22. The method of paragraph D21, further comprising receiving a health data reading generated from the one or more pressure of blood readings by the computer system.

D23. The method of paragraph D1, further comprising attaching the pressure of blood monitor to a finger, the pressure of blood monitor being part of a ring system that includes a printed circuit board coupled to the pressure of blood monitor.

E1. A method for monitoring pressure of blood in an artery, comprising:
contacting a non-inflatable sensor of a blood pressure monitoring device at an area above an artery of a finger,
collecting with the non-inflatable sensor one or more pressure of blood data readings from the area after the contacting and after a pressure is exerted at the area on the sensor; and
analyzing with a computer device one or more pressure data readings to generate at least one of a blood pressure reading and a heart pulse reading.

F1. A system to monitor the pressure of blood, comprising:
a monitoring device that includes a capacitive sensor, the capacitive sensor being configured to be in contact with an area of skin above an artery, the capacitive sensor including:

a conductive element disposed on a bottom side adjacent a printed circuit board, a resilient member, an insulation layer separating the conductive element from the resilient member, and an adhesive layer covering the resilient member, wherein the capacitive sensor is configured to collect one or more pressure of blood data readings while in contact with the area; and a data processing device, in communication with the capacitive sensor, configured to analyze data readings produced by the sensor, the data processing device including a processor, a memory, and a set of instructions stored in the memory and executed by the processor to determine whether the information provided by the sensor meets selected criteria, and providing an alert to a user if the information meets the criteria.

F2. The system of paragraph F1, wherein the sensor is configured to sense a pressure parameter associated with at least one of a blood pressure rate and a heart pulse rate.

F3. The system of paragraph F1, wherein the monitoring device includes an attachment portion that houses the sensor, the attachment portion being configured such that bending a finger causes pressure to be exerted on the sensor from the finger.

F4. The system of paragraph F1, wherein the sensor is a proportional sensor.

F5. The system of paragraph F1, wherein the resilient member is a spring deformable by pressure.

F6. The system of paragraph F5, wherein the capacitive sensor measures changes in capacitance in response to changes in pressure.

F7. The system of paragraph F5, wherein the corrugated leaf spring forms a component of a capacitor.

F8. The system of paragraph F1, wherein the conductive elements comprises copper and gold.

F9. The system of paragraph F1, further including an indicator in communication with the sensor, the indicator providing a signal when sensed blood pressure meets a selected criterion.

F10. The system of paragraph F9, wherein the monitoring device is configured to create pressure on an artery in the finger when a user bends the finger.

G1. A method for monitoring pressure of blood in an artery, comprising:

contacting a non-invasive sensor of a pressure of blood monitoring device at an area above an artery of a finger, collecting with the sensor one or more pressure data readings, other than readings corresponding to an air pressure reading, from the area after the contacting and after a pressure is exerted at the area on the sensor; and analyzing with a computer device one or more pressure data readings to generate at least one of a blood pressure reading and a heart pulse reading.

G2. The method of paragraph G1, wherein analyzing with a computer device one or more pressure data readings does not include analyzing any pressure data readings corresponding to an air pressure reading.

G3. The method of paragraph G1, wherein the pressure exerted at the area is caused by a bending of the finger, the bending causing a high pressure in the artery, relative to a lesser bending position, and the bending causing a liquid injection adjacent the area.

G4. The method of paragraph G1, wherein the pressure exerted at the area is caused by the finger bending at a proximal inter-phalangeal (PIP) joint.

G5. The method of paragraph G1, further comprising collecting at continuous time intervals one or more pressure readings while the finger is bending from a first position to a bent position.

G6. The method of paragraph G1, further comprising collecting at continuous time intervals one or more pressure data readings while the finger is bending from a bent position to another bending or an unbent position.

G7. The method of paragraph G1, further comprising automatically activating the sensor to collect one or more pressure data readings in response to a bending of the finger.

G8. The method of paragraph G1, further comprising continuously monitoring with the sensor the area when the finger is in a position where the exerted force is zero mmHg.

G9. The method of paragraph G1, wherein contacting a non-invasive sensor of a pressure of blood monitoring device at an area above an artery of a finger includes contacting the area above the artery on a side of a finger between a metacarpophalangeal (MCP) joint and a proximal inter-phalangeal (PIP) joint.

G10. The method of paragraph G1, further comprising receiving at least one of the blood pressure reading and the heart pulse reading generated based on the one or more pressure data readings analyzed by the computer system.

G11. The method of paragraph G1, further comprising attaching the pressure of blood monitoring device to a finger, the pressure of blood monitoring device being part of a ring system that includes a printed circuit board coupled to the non-invasive sensor.

G12. The system of paragraph G1, wherein the non-invasive sensor is a proportional sensor.

G13. The system of paragraph G1, wherein the non-invasive sensor is a capacitive sensor, and further comprising measuring changes in capacitance in response to changes in pressure to generate the one or more pressure data readings.

G14. The method of paragraph G1, further comprising: providing a sensor capable of detecting the exerted pressure such that the sensor is in an inactive state when the exerted pressure is less than a first level and is in an active state when the exerted pressure is at a second level, higher than the first level, and generating an indicator when the exerted pressure is between a diastolic pressure and a systolic pressure.

H1. A method for monitoring pressure of blood in an artery, comprising:

contacting a capacitive sensor of a pressure monitoring device at an area of a body capable of being monitored for pressure of blood readings, collecting with the capacitive sensor one or more pressure data readings from the area after the contacting and after a pressure is exerted at the area on the sensor; and analyzing with a computing device the one or more pressure data readings to generate one or more health data readings based on an analysis of the one or more pressure data readings.

H2. The method of paragraph H1, further comprising collecting a plurality of pressure data readings continuously as the exerted pressure changes between 0 millimeters of mercury (mmHg) and 300 mmHg.

H3. The method of paragraph H1, further comprising continuously collecting readings over a plurality of time intervals, every approximately 100 milliseconds, as the exerted pressure changes between approximately 40 mmHg and approximately 180 mmHg, further wherein changing the exerted pressure continuously between zero mmHg and 300 mmHg occurs over approximately 30 seconds.

H4. The method of paragraph H1, further comprising analyzing the plurality of pressure data readings to generate a blood pressure reading as the health data reading.

H5. The method of paragraph H1, further comprising measuring an oscillation of pressure data readings over time intervals of the collected plurality of pressure readings to generate a heart pulse rate as the health data reading.

H6. The method of paragraph H1, further comprising automatically collecting a plurality of pressure data readings continuously as the exerted pressure changes while in the range of greater than zero millimeters mercury (mmHg) and less than or equal to 300 mmHg.

H7. The method of paragraph H1, further comprising:
monitoring the area continuously with the capacitive sensor, and
automatically collecting at least one reading after detecting with the capacitive sensor a change in pressure at the area from a zero mmHg state to a non-zero mmHG state.

H8. The method of paragraph H1, further comprising analyzing a change in capacitance of the capacitive sensor to generate the one or more pressure data readings, wherein analyzing a change in capacitance includes measuring a change in a configuration between conductive materials of the capacitive sensor.

H9. The method of paragraph H1, wherein measuring the one or more pressure of blood readings occurs without data generated from an air inflatable element.

H10. The method of paragraph H1, wherein contacting a capacitive sensor of a blood pressure monitoring device at an area of a body capable of being monitored for pressure of blood readings includes contacting the area above an artery of a finger.

H11. The method of paragraph H1, further comprising providing the capacitive sensor configurable to be in contact with the area of skin above an artery, the capacitive sensor including:
a conductive element disposed on a bottom side adjacent a printed circuit board,
a resilient member,
an insulation layer separating the conductive element from the resilient member, and
an adhesive layer covering the resilient member,
wherein the capacitive sensor is configured to collect one or more pressure of data readings while in contact with the area; and
a data processing device, in communication with the capacitive sensor, configured to analyze data readings produced by the sensor, the data processing device including a processor, a memory, and a set of instructions stored in the memory and executed by the processor to determine whether the information provided by the sensor meets selected criteria, and providing an alert to a user if the information meets the criteria.

H12. The system of paragraph H11, further comprising providing the pressure monitoring device with an attachment portion that houses the sensor, and
bending of a finger causes pressure to be exerted on the sensor from the finger.

Advantages, Features, Benefits

The different embodiments of the blood pressure monitor described herein provide several advantages over known solutions for monitoring and measuring blood pressure. For example, the illustrative embodiments of a pressure of blood monitor, such as a finger-mounted pressure of blood monitor, described herein allow pressure to be exerted on an artery without use of cumbersome inflatable cuffs and associated equipment and power sources. Any of the one or more embodiments may be configured to monitor any area of the body capable of being monitored for pressure of blood. Additionally, and among other benefits, illustrative embodiments of the pressure of blood monitor described herein allow both on-demand and continuous monitoring of pressure of blood, and may be more accurate than previous methods. No known system or device can perform these functions, particularly in a finger-mounted, low-cost fashion. Thus, the illustrative embodiments described herein are particularly useful for patients needing continuous, low-cost monitoring, particularly in the home. However, not all embodiments described herein provide the same advantages or the same degree of advantage.

CONCLUSION

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Furthermore, explicit reference is hereby made to all inventions shown in the drawings, whether or not described further herein.

What is claimed is:

1. A method for monitoring pressure of blood in an artery, comprising:
positioning a non-invasive blood pressure (BP) monitoring device on a finger, wherein the BP monitoring device comprises a pressure sensor mounted to a brace configured to span a phalanx bone of the finger, and wherein positioning the BP monitoring device includes securing the brace to the finger using a non-stretchable strap, such that the pressure sensor of the BP monitoring device contacts an area above an artery of the finger;
causing soft tissue of the finger to press against the pressure sensor by causing the finger to bend, such that a variable pressure is applied to the pressure sensor as a result of causing the finger to bend;
in response to sensing, by the pressure sensor, a nonzero pressure applied to the pressure sensor as a result of the bending of the finger, sensing, using the pressure sensor in contact with the area above the artery of the finger, one or more pressure data readings, each of the one or more pressure data readings corresponding to a compression of the pressure sensor caused by blood pressure in the artery; and
calculating one or both of a blood pressure value and a heart pulse rate based on an oscillometric analysis of the one or more pressure data readings by a data processing system in electronic communication with the pressure sensor.

2. The method of claim 1, wherein the one or more pressure data readings exclude any pressure data readings corresponding to an air pressure.

3. The method of claim 1, wherein the finger is caused to bend at a proximal inter-phalangeal (PIP) joint.

4. The method of claim 1, wherein causing the finger to bend includes causing the finger to bend from an unbent position to a bent position.

5. The method of claim 1, wherein the one or more pressure data readings are sensed while the finger is bending from a bent position to another bent position or to an unbent position.

6. The method of claim 1, wherein positioning the BP monitoring device on the finger includes positioning the pressure sensor above the artery on a side of the finger between a metacarpophalangeal (MCP) joint and a proximal inter-phalangeal (PIP) joint.

7. The method of claim 1, wherein the BP monitoring device is part of a ring system that includes a printed circuit board coupled to the pressure sensor.

8. The method of claim 1, wherein the pressure sensor comprises a proportional sensor configured such that a property of the proportional sensor changes linearly in response to a change in the compression of the pressure sensor caused by blood pressure in the artery.

9. The method of claim 1, wherein the pressure sensor comprises a capacitive sensor, and sensing the one or more pressure data readings includes measuring a change in capacitance based on compression of the pressure sensor.

10. A method of monitoring pressure of blood in an artery, comprising:
    positioning a pressure sensor of a non-invasive blood pressure (BP) monitoring device on a finger such that bending the finger causes soft tissue of the finger to press against the pressure sensor;
    in response to detection by the pressure sensor of a nonzero pressure corresponding to a compression of the pressure sensor caused by blood in the artery based on a pressure applied to the artery by bending the finger from a first position to a second position,
    sensing one or more pressure data readings each corresponding to a compression of the pressure sensor caused by blood in the artery as the finger varies the pressure applied to the artery by bending from the second position to a third position; and
    calculating one or both of a blood pressure value and a heart pulse rate based on an oscillometric analysis of the one or more pressure data readings by a data processing system in electronic communication with the pressure sensor.

11. The method of claim 10, wherein the finger is unbent in the first position.

12. The method of claim 10, wherein the pressure sensor is mounted to a brace secured to the finger by a non-stretchable strap such that the brace spans a phalanx bone of the finger.

13. The method of claim 12, wherein the data processing system is secured to the finger by the non-stretchable strap.

14. The method of claim 12, wherein positioning the pressure sensor on the finger includes positioning the pressure sensor above the artery on a side of the finger between a metacarpophalangeal (MCP) joint and a proximal inter-phalangeal (PIP) joint.

15. A method of monitoring pressure of blood using a pressure sensor mounted on a finger of a patient, the method comprising:
    sensing, as the finger bends from a first position to a second position, a threshold pressure corresponding to a compression of the pressure sensor caused by blood in an artery of the finger;
    in response to sensing the threshold pressure, sensing one or more pressure data readings each corresponding to a compression of the pressure sensor by blood in the artery as the finger increases a pressure on the artery by bending from the second position to a third position; and
    calculating a cardiac property of the patient based on an oscillometric analysis of the one or more pressure data readings by a data processing system in electronic communication with the pressure sensor.

16. The method of claim 15, wherein the artery is occluded when the finger is in the third position.

17. The method of claim 15, wherein the finger is unbent in the first position, such that bending the finger from the first position to the second position increases a pressure applied to the artery by soft tissue of the finger from zero pressure to a nonzero pressure corresponding to the threshold pressure sensed by the pressure sensor.

18. The method of claim 17, wherein the pressure sensor is coupled to a brace spanning a phalanx bone of the finger, and the brace is secured to the finger by a non-stretchable strap.

19. The method of claim 18, wherein the brace is secured to the finger such that the pressure sensor is disposed above the artery on a side of the finger between a metacarpophalangeal (MCP) joint and a proximal inter-phalangeal (PIP) joint.

20. The method of claim 19, wherein the data processing system is mounted on the finger by the brace.

21. The method of claim 20, wherein the cardiac property includes one or both of a blood pressure value and a heart pulse rate.

* * * * *